(12) United States Patent
Sturgill et al.

(10) Patent No.: US 8,952,048 B2
(45) Date of Patent: Feb. 10, 2015

(54) TREATMENT OF IMMUNE DISORDERS USING KAINATE RECEPTOR ANTAGONISTS

(75) Inventors: Jamie Lynn Sturgill, Richmond, VA (US); Daniel Harper Conrad, Midlothian, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 13/574,808

(22) PCT Filed: Jan. 25, 2011

(86) PCT No.: PCT/US2011/022353
§ 371 (c)(1),
(2), (4) Date: Oct. 22, 2012

(87) PCT Pub. No.: WO2011/091401
PCT Pub. Date: Jul. 28, 2011

(65) Prior Publication Data
US 2013/0046005 A1    Feb. 21, 2013

Related U.S. Application Data

(60) Provisional application No. 61/297,874, filed on Jan. 25, 2010.

(51) Int. Cl.
*A61K 31/40* (2006.01)
*A61K 31/404* (2006.01)
*A61K 31/42* (2006.01)
*G01N 33/50* (2006.01)
*G01N 33/564* (2006.01)
*A61K 38/00* (2006.01)

(52) U.S. Cl.
CPC ............... *A61K 31/40* (2013.01); *A61K 31/404* (2013.01); *A61K 31/42* (2013.01); *G01N 33/5052* (2013.01); *G01N 33/564* (2013.01); *A61K 38/00* (2013.01); *G01N 2800/56* (2013.01)
USPC ......................................................... 514/411

(58) Field of Classification Search
CPC .. A61K 31/403; A61K 31/404; A61K 31/198
See application file for complete search history.

(56) References Cited

U.S. PATENT DOCUMENTS

| | | | | |
|---|---|---|---|---|
| 5,198,461 A | * | 3/1993 | Watjen et al. | 514/411 |
| 5,446,051 A | * | 8/1995 | Ornstein | 514/307 |
| 6,156,794 A | * | 12/2000 | Faiman et al. | 514/478 |

OTHER PUBLICATIONS

Tasker et al. Canadian Journal of Physiology and Pharmacology, 1996, vol. 74, No. 9, pp. 1047-1054 (Abstract attached).*

* cited by examiner

*Primary Examiner* — James D Anderson
(74) *Attorney, Agent, or Firm* — Whitham Curtis Christofferson & Cook, PC

(57) ABSTRACT

Allergies and immune system disorders (e.g. autoimmune diseases) are treated by administration of an agent that blocks activation of the kainic acid receptor (KAR) in B cells. The agents include antagonists and weakly activating agonists.

5 Claims, 13 Drawing Sheets

TREATMENT OF IMMUNE DISORDERS USING KAINATE RECEPTOR ANTAGONISTS

CROSS-REFERENCE TO RELATED APPLICATIONS

This application is a Rule 371 national stage application of International Application PCT/US2011/022353 filed Jan. 25, 2011, and that application claims priority U.S. Provisional Application Ser. No. 61/297,874 filed Jan. 25, 2010.

BACKGROUND OF THE INVENTION

1. Field of the Invention

The invention generally relates to the treatment of immune related disorders. In particular, the invention provides methods of reducing the symptoms associated with immune related disorders by administering agents that are antagonists of kainate receptors.

2. Background of the Invention

Immune system related disorders have deleterious health effects ranging from the mildly annoying (e.g. some allergy symptoms) to severely debilitating and/or life threatening (e.g. anaphylactic shock, autoimmune diseases such as rheumatoid arthritis, and systemic lupus erythematosus (SLE)). Such conditions are generally attributable to over-activity of the immune system. A common characteristic that has been identified for several immune system disorders is the presence of elevated levels of glutamate in the periphery of patients with such disorders. In fact, some other diseases that are not usually thought of as immune related (e.g. certain cancers, epilepsy, etc.) are also characterized by elevated levels of glutamate.

While there has been some success in treating immune related disorders, no cures have been developed, and some treatments have undesirable side effects and/or do not provide full relief from symptoms of the disease. There is thus an ongoing need to provide new methods of treating immune related disorders.

SUMMARY OF THE INVENTION

It has been discovered that kainate receptors, which are activated by the binding of glutamate, are present on lymphocyte cells of the immune system. Binding of the natural ligand glutamate to kainate receptors (KARs) on lymphocyte cells activates the receptors and initiates immune system pathways that ultimately result in B-cell proliferation and increased levels of IgG and IgE production. Thus, elevated levels of glutamate associated with immune system disorders are the likely causative agent of immune system over-activity which is characteristic of many immune system disorders. In fact, as demonstrated herein, suppression of glutamate binding to KARs of lymphocytes by exposing the KARs to an antagonist prevents glutamate binding and results in suppression of B-cell proliferation and IgG and IgE production. Thus, the administration of agents that are KAR antagonists can be used to treat disorders or conditions characterized by high levels of glutamate, including various allergies, various autoimmune disorders, and others.

It is an object of this invention to provide a method of treating an allergy or an autoimmune disease in a patient in need thereof. The method comprises the step of administering to the patient at least one agent that is an antagonist of a kainate receptor (KAR) of a B cell. The at least one agent is administered in a form and under conditions which permit binding to the KAR, and which prevent or reduce glutamate binding to the KAR, so as to reduce B cell proliferation in the patient. In some embodiments, the autoimmune disease is selected from the group consisting of systemic lupus erthyematosus (SLE), rheumatoid arthritis, and Sjogren's syndrome. In other embodiments, the at least one agent is selected from the group consisting of NS-102 and glutamate mimics or analogs. In some embodiments, the method further comprises the step of identifying a patient with symptoms of an allergy or an autoimmune disease prior to the step of administering. In other embodiments, the method includes the step of monitoring symptoms of the allergy or the autoimmune disease after the step of administering.

The invention also provides a method of inhibiting or reducing B-cell proliferation in a patient in need thereof. The method includes the step of administering to the patient at least one agent that is an antagonist of a kainate receptor. The at least one agent is administered in a form and under conditions which permit binding to the KAR, and which prevent or reduce glutamate binding to the KAR, so as to reduce B cell proliferation in the patient. In one embodiment, the agent is selected from the group consisting of NS-102 and glutamate mimics or analogs.

The invention also provides a method of inhibiting one or more of B-cell activation, proliferation and isotype switching in vivo. The method comprises the step of contacting in vivo B-cells with at least one agent that is an antagonist of a kainate receptor. The at least one agent is in a form which permits binding to the KAR and the step of contacting occurs under conditions which permit the at least one agent to bind to the KAR and prevent or reduce glutamate binding to the KAR, so as to inhibit one or more of B-cell activation, proliferation and isotype switching. In one embodiment, the at least one agent is selected from the group consisting of NS-102 and glutamate mimics or analogs.

The invention also provides a method of treating a patient suffering from a condition associated with elevated levels of IgG or IgE. The method comprised the step of administering to said patient at least one agent that is an antagonist of a kainate receptor, wherein said at least one agent is administered in a form and under conditions which permit binding to kainate receptor (KAR), and which prevent or reduce glutamate binding to said KAR, so as to reduce B cell production of IgG or IgE in said patient. In some embodiments, the condition is selected from the group consisting of HIV, epilepsy, an autoimmune disease, and exposure to corticosteroids. In some embodiments, the at least one agent is selected from the group consisting of NS-102 and glutamate mimics. In some embodiments, the method includes the step of identifying a patient suffering from a condition associated with elevated levels of IgG or IgE prior to the step of administering. In other embodiments, the method includes the step of monitoring levels of IgG or IgE in the patient after the step of administering.

DETAILED DESCRIPTION

Figure 1A:
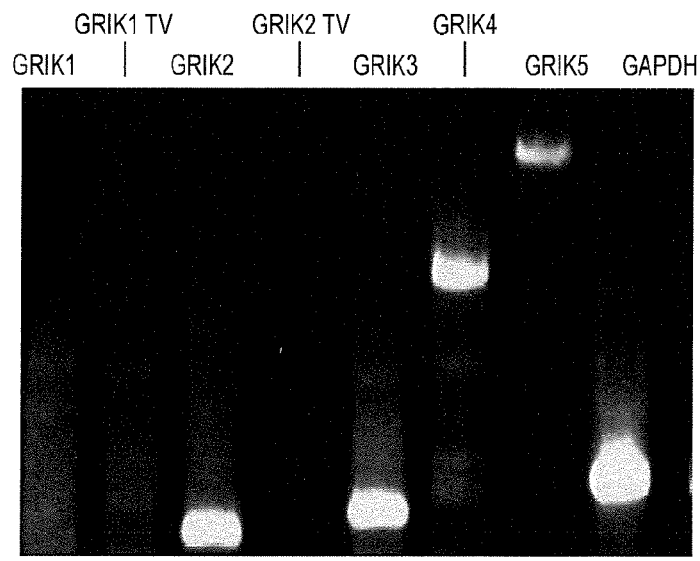
FIG. 1A-C. Kainate receptors are expressed in the human immune system. Human B cells were analyzed for the presence of kainate receptor subunits both at the RNA and protein level. (A) The human cell line RPMI8866 was examined by RT-PCR for the presence of multiple subunits of the kainate receptor. A representative agarose gel of three performed is shown. (B) Western blot shows presence GluK4 protein in multiple B cell sources. (C) Flow cytometry of human leukocytes shows both presence of protein as well as cell surface expression of KARs based on GluK4 expression.

The invention provides methods to treat conditions or diseases characterized by the presence of high glutamate levels (e.g. allergies and auto-immune disorders) by administering one or more KAR antagonists. Without being bound by theory, it is believed that competitive binding of an antagonist to the KAR prevents the occupation of the receptor by glutamate and hence lowers the percentage of receptors that are occupied by glutamate. As a result, fewer KARs are activated, and downstream immune system pathways such as proliferation of B cells, isotype switching and production of IgG and IgE are also not activated, resulting in prevention or lessening of disease symptoms.

By "antagonist" we mean a compound which binds to the KAR receptor and, when bound, prevents the binding of other ligands such as glutamate. Antagonists generally bind at or near the binding site of a ligand with which they compete, sterically occluding the site and thus preventing binding of the other ligand. Those of skill in the art will recognize that in biological systems, such binding is generally not completely irreversible, although in some cases it may be. The binding of the antagonist may be essentially irreversible or somewhat, (or even readily) reversible, so long as the binding of the antagonist is sufficient to result in antagonist displacement of glutamate from a sufficient number or fractional percentage of receptors to result in amelioration of disease symptoms of the disease being treated. Generally, the affinity of such an antagonist will be in the range of from about 1 µm to about 1000 µm, and preferably in the range of from about 10 µm to about 100 µm.

The binding of an antagonist to KAR results in a lack of activation (or at least reduced activation) of KAR, and hence a decrease in the cellular events which would otherwise ensue. For example, the level of B-cell activation and proliferation is generally decreased, e.g. by at least about 10%, 20%, 30%, 40%, 50%, 60%, 70%, 80%, or even by about 90% or 95% or more (e.g. up to about 100%, i.e. complete) inhibition. As a result of the decrease in B-cell activation and proliferation, B cell isotype switching is prevented, and the amount of IgG and IgE that is produced is reduced, e.g. by at least about 10%, 20%, 30%, 40%, 50%, 60%, 70%, 80%, or even by about 90% or 95% or more (e.g. up to about 100%). These reductions cause a decrease in disease symptoms which may be of a similar magnitude.

"Isotype switching" refers to class switching which occurs after activation of a mature B cell via its membrane-bound antibody molecule (or B cell receptor) to generate a different class of antibody than was previously generated. This phenomenon is also referred to as "immunoglobulin class switching" or isotypic commutation" or "class switch recombination" and is a biological mechanism that changes a B cell's production of antibody from one class to another, for example, from IgM to IgG.

Examples of KAR antagonists that may be administered using the methods of the invention include but are not limited to NS102 (5-Nitro-6,7,8,9-tetrahydro-1H-benzo[g]indole-2,3-dione 3-oxime); glutamate derivatives (e.g. pyrrolidine-, isoxazole-, oxa(thia)diazole-, pyrimidine-, and hexahydrofuropyrane derivatives); thienol[2,3-d]pyrimidines; 2-aminothiophene-3-carboxylic acid derivatives such as ethyl 2-amion-4-methyl-5-phenylthiophene-3-carboxylate (see Briel et al. 2010 and references therein); LU97175 and IEM-1754 (see Kaczor 2009 and references therein); and those that are described in issued U.S. Pat. Nos. 5,446,051 and 6,156,794, the complete contents of which are herein incorporated by reference; etc. Preferably, the agents (e.g. antagonists) that are used in the practice of the invention are specific for the KAR (Le, they bind only this receptor and no other) or selective for binding to the KAR (they bind the KAR in preference to any other receptor by at least a factor of 5, 10, 20, 30, 40, 50, 60, 70, 80, 90 or 100 or greater (e.g. several hundred or even 100-fold), i.e. which bind to the receptor with at least 5, 10, etc. fold higher affinity than to other receptors.

KAR antagonists are generally administered in a pharmaceutical composition. The compositions generally include one or more substantially purified KAR antagonists as described herein and a pharmacologically suitable carrier. The preparation of such compositions is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other adjuvants. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of KAR antagonist in the formulations may vary. However, in general, the amount in the formulations will be from about 1-99%.

The KAR antagonist compositions may be administered by any of the many suitable means which are well known to those of skill in the art, including but not limited to by injection, inhalation, orally, intravaginally, intranasally, by ingestion of a food or probiotic product containing the KAR antagonist, topically, as eye drops, via sprays, incorporated into dressings or bandages (e.g. lyophilized forms may be included directly in the dressing), etc. In preferred embodiments, the mode of administration is topical or orally or by injection.

Generally, the amount of KAR antagonist that is administered is that which is sufficient to safely ameliorate symptoms of the immune disorder. This is generally determined by a skilled practitioner, e.g. a physician or other clinician, and is generally an amount in the range of from about 1 to about 100 mg/kg. In other embodiments, the amount may be that which results in a level in the circulatory system of the patient in the range of from about 100 to about 5 µmolar and preferably from about 50 to about 10 µmolar.

In some embodiments, various analogs, mimics or mimetics of glutamate are used in the practice of the invention, e.g. small molecules which comprise at least the portion of the glutamate structure which binds to the KAR, or which comprise analogous atoms which "fit" the binding site, but which do not activate the receptor, or which activate the receptor to a lesser extent. Exemplary modifying groups include but are not limited to pyrrolidine-, isoxazole-, oxa(thia)diazole-, pyrimidine-, and hexahydrofuropyrane. In addition, various analogs, mimics or mimetics of kainic acid (KA) may also be used, e.g. small molecules which comprise at least the portion of the KA structure which binds to the KAR, or which comprise analogous atoms which "fit" the binding site, but which do not activate the receptor, or which activate the receptor to a lesser extent. In addition, as is well known to those of skill in the art, various "small molecule" ligands may be designed, evaluated and selected for their ability to bind to the KAR. Those of skill in the art are well acquainted with the design of such molecules and their screening for binding activity. Briefly, small molecules are designed which contain one or more known features of ligands which are known to bind to a receptor, or which are suspected of binding to a receptor (e.g. because they bind to a related receptor), or which bind to a site on the receptor that is likely to block the binding of glutamate. A variety of molecules are built up "in silico" starting with what are considered to be the most essential or most desired features of a ligand, and likely candidates are chemically synthesized. Once synthesized, large families of such molecules can be screened using any of several receptor screening methods known to those of the art. Successful candidates (e.g. those with at least some affinity for the receptor) are then further tested (e.g. in vitro using cell culture, and then in animal models) for their ability to bind the receptor without activating it, and to reduce disease symptoms.

While in some embodiments, the compound that is administered is an antagonist of KAR, this need not always be the case. In other embodiments, compounds that function as agonists (compounds that hind to and activate the KAR) may also be used, so long as they effectively compete with glutamate binding to the KAR and exhibit a lower level of activation of the KAR than glutamate, e.g. a level that is low enough to result in a decrease of disease symptoms.

In yet other embodiments, the agent that is administered is an antibody to the KAR receptor, particularly to one or more of the GRIK2, GRIK3, GRIK4, and GRIK5 subunits, and even more particularly to the GRIK4 subunit that is required for binding.

The antagonists that are used in the practice of the invention may be used in conjunction with other agents that are used to treat immune disorders, examples of which include but are not limited to antihistamines, corticosteroids, antileukotriene inhibitors for allergies, and anti TNF alpha blockers for arthritis.

Immune disorders that are caused by or related to B-cell over-proliferation include but are not limited to: allergies (e.g. hay fever, allergies to various fruits and vegetables, pet allergies, asthma, etc.; rheumatoid arthritis; systemic lupus erythematosus (SLE); psoriasis; multiple myelomas, B cell cancers, etc.

The methods of the invention involve identifying patients in need of the therapies provided herein, and then administering at least one KAR antagonist to such a patient. Those of skill in the art are familiar with symptoms which indicate that a patient is suffering from an immune related disorder. For example, symptoms of allergies include but are not limited to sneezing, itching and watering of eyes and or nasal passages, swelling, welts, etc. Symptoms of rheumatoid arthritis include but are not limited to inflammation, fatigue, loss of energy, lack of appetite, low-grade fever, muscle and joint aches, and stiffness, etc. Symptoms of SLE include fever, malaise, joint pains, myalgias, fatigue, and temporary loss of cognitive abilities, rash, joint pain, and anemia. A trained clinician assesses the patient symptoms and in some cases, further more invasive tests (e.g. blood analysis) are carried out in order to confirm a diagnosis.

Several methods may be used to detect and measure the efficacy of the treatment methods described herein. In some embodiments, the clinical outcome of administration is monitored/measured, e.g. symptom amelioration such as decreased sneezing, itching, headache, pain associated with movement, lack of energy, lowered temperature, etc. In other embodiments, more invasive tests may be used, e.g. blood or other tissue samples may be used to analyze B-cell or IgG levels, lung function for asthma, skin examination, and kidney function tests for SLE. To be considered effective, deleterious symptoms generally decrease by at least about 10%, 20%, 30%, 40%, 50%, 60%, 70%, 80%, or even by about 90% or 95% or more (e.g. up to 100%, i.e. complete disappearance of symptoms). Even partial lessening of symptoms may be highly beneficial to the patient. Further, since immune disorders are complex, some symptoms may be alleviated while other may persist, yet this may still be a worthwhile clinical outcome for the patient. The results of administration are generally monitored throughout the course of treatment.

The invention also provides methods of treating patients identified as suffering from a condition associated with elevated levels of IgE e.g. HIV, epilepsy, an autoimmune disease, exposure to corticosteroids, etc. Levels of IgG and IgE in a patient may be determined by ELISA assays. Elevation of levels is determined by comparison to the levels present in normal control subjects, and normally exceeds the normal level by at least 25%, or 50%, or even more. Generally, levels of IgG and IgE in the patient are then monitored after administration of an agent that blocks activation of the KAR receptor, e.g. an antagonist or weakly activating agonist. Monitoring continues throughout the course of treatment.

The methods of the invention are generally used to treat mammals, usually humans, although this need not always be the case. Veterinary applications are also contemplated.

EXAMPLES

Example 1

Kainate Receptor Signaling Enhances Immunoglobulin Synthesis

CD23 (FCeRII) is a type II integral membrane protein and the low affinity receptor for IgE. Through studies using knock-out and transgenic animals, CD23 has been implicated as a natural, negative regulator of IgE production. Although the mechanism remains unclear, interactions with cell surface CD21 as well as direct signaling by the membrane form of CD23 have both been hypothesized to be responsible for IgE modulation. A soluble monomeric form of CD23 (sCD23) is released following proteolytic cleavage by a disintegrin and metalloprotease 10 (ADAM10) (Weskamp et al., 2006). Enhanced CD23 cleavage has been shown to correlate with increased IgE production in both mouse and human. In addition to its effects on allergic disease, sCD23 has been linked to the activation of macrophages, via interaction with CD11b/CD18 or CD11c/CD18, resulting in the release of pro-inflammatory mediators and the onset of inflammatory disease.

In view of the recent demonstration that ADAM10 is the primary CD23 sheddase, we searched for agents that would modify ADAM10 activity. The overall purpose was to test the hypothesis that ADAM 10 modulation would, by virtue of being the CD23 sheddase, result in IgE modulation. Ortiz et al. showed that when a specific type of glutamate receptor, namely the kainate receptor (KAR), was stimulated with its ligand, ADAM10 mRNA increased (Ortiz et al., 2005). KARs are one of three types of multi-subunit, ionotropic glutamate receptors which are named based upon their preferred pharmacological ligand: α-amino-3-hydroxy-5-methyl-4-isoxazole propionic acid (AMPA), N-methyl-D-aspartic acid (NMDA), and kainic acid (KA). KARs are the most recently identified of the three and have been shown to be widely expressed in the central nervous system (CNS) (Chittajallu et al., 1999; Lerma, 2006), however, little is reported on their presence outside the CNS. Kainic acid, a chemical first isolated from the red algae Digenea simplex, is a potent agonist of KARs and is a widely used for the generation of epilepsy in laboratory rodent models due to its ability to cause neuroinflammation following epilepsy induction.

Glutamate, the major excitatory neurotransmitter in the CNS has recently been implicated in a variety of diseases. For example, it has been shown that patients with certain cancers (Eck et al., 1990), human immunodeficiency virus (HIV) (Eck et al., 1989), epilepsy (Rainesalo et al., 2004), autism (Aitken, 2008), and certain autoimmune illnesses such as rheumatoid arthritis (RA) (McNearney et al., 2000), and systemic lupus erythematosus (SLE) (West, 2007) all have elevated levels of glutamate in the periphery. Interestingly, autoimmune disease treatments which include corticosteroid use can also increase peripheral glutamate levels (Borsody and Coco, 2001; Raber, 1998; Eck et al., 1990). While glutamate receptor signaling has been examined in T cells (Ganor et al., 2003a) and macrophages (Boldyrev et al., 2004), there are currently no published observations on the effects of glutamatergic stimuli on B cells.

This example shows that human B cells do indeed express the kainate receptor. KAR activation was found to increase ADAM10 expression and activity, as measured by sCD23 release. A significant increase in B cell proliferation and Ig production was also seen with both purified B cells and PBMC. The implications of this finding for human allergic and autoimmune diseases are discussed; and this invention utilizes this finding to provide effective therapy for human allergic and autoimmune diseases.

Materials and Methods

Media, Reagents, and Cell Lines. All cells were grown in complete culture medium as indicated (CRPMI-10 or CDMEM-10; RPMI-1640 or Dulbecco's Modified Eagle Medium containing 10% heat inactivated (56° C., 30 min) fetal bovine serum (Gemini Bio-Products, West Sacramento, Calif.), 2 mM L-glutamine, 50 µg/ml penicillin, 50 µg/ml streptomycin, 1 mM sodium pyruvate, 50 µg/ml amphotericin B, 50 µM 2-mercaptoethanol and 20 mM HEPES buffer (all from Invitrogen Carlsbad, Calif.)). All lines are kept in confluent culture under log phase growth in complete culture medium at 37° C. in humidified air with 5% $CO_2$. Kainic Acid (KA), dimethylsulfoxide (DMSO), L-glutamic acid (Glu), and antagonists (topiramate (TPM), NS102 and NBQX) were all purchased from Sigma (St. Louis, Mo.). Human IL-21 and mouse antihuman CD40 (clone G28-5) (American Type Culture Collection, (ATCC), Manassas, Va.) were generated in our laboratory as previously described (Caven et al., 2005a). rhIL-4 was purchased from R&D Systems (Minneapolis, Minn.). The ADAM10 selective inhibitor INCB008765 was kindly provided by Incyte Corporation, Wilmington, Del. (Fridman et al., 2007; Zhou et al., 2006). *Human Cells*. Human tonsils were obtained from routine tonsillectomies at Henrico Doctors Hospital (Richmond, Va.) or the VCU Tissue Data Acquisition and Analysis Core (TDAAC). Tonsils were placed in media supplemented with antibiotics and mechanically disrupted using a Seward Stomacher 80 Biomaster Lab Blender (Brinkmann, Westbury, N.Y.) at normal speed for 60 seconds. To obtain a single cell suspension, the resulting product was underlayed with Ficoll-Hypaque (GE Healthcare Piscataway, N.J.). Following centrifugation (20 min at 400× g), the cells at the interface were removed and washed in PBS. To isolate B cells, the tonsilar cells were incubated with a FITC-anti-human IgD (BD Pharmingen San Diego, Calif.) for 30 min on ice and B cells were isolated by using the Miltenyi anti-FITC Microbeads, per manufacturer's instructions (Miltenyi Biotec Auburn, Calif.) Final B cell preparations were >95% pure IgD+ by FACS analysis.

Alternatively when whole PBMC was used, buffy coats were obtained from the Virginia Blood Service Center (Richmond, Va.). PBMC were isolated by Ficoll gradient density centrifugation. All human studies research was performed in accordance to the Virginia Commonwealth University Institution Review Board per approved protocols. RT-PCR and qPCR. RNA was isolated via standard Trizol (Invitrogen) purification protocol and the Access Quick RT-PCR kit (Promega, Madison Wis.) was used with gene specific primers to examine for the presence of kainate receptor subunits and their transcript variants. Primers were designed using VectorNTI software (Invitrogen). Ready-made Primers® for G3PDH and all custom made primers for all sequences were synthesized by Integrated DNA Technologies (Coralville, Iowa). qPCR experiments were performed by the nucleic acid core in the ABI Prism® 7900 Sequence Detection System (Applied Biosystems, Foster City, Calif.) using the TaqMan® One Step PCR Master Mix Reagents Kit. All the samples were tested in triplicate using the following conditions: 48° C./30 min; 95° C./10 min; and 40 cycles of 95° C./15 sec and 60° C./1 min. The cycle threshold was determined to provide the optimal standard curve values (0.98 to 1.0). The probes and primers for ADAM10 (#Hs00153853_m1) were purchased from ABI. Human beta actin primers were from the Pre-developed TaqMan® Assay Reagents and were used as endogenous control. Relative ADAM10 mRNA is determined as a relative ratio based upon beta-actin.

Western Blot.

Five million cells were lysed in Hepes Buffered Saline (HBS) with 1% NP-40 on ice for 10 minutes. Nuclei were removed by centrifugation and cytosolic proteins were treated with SDS buffer and heated at 70° C. for 10 minutes. Proteins were run on an MES NuPage gel (Invitrogen) and then transferred to nitrocellulose. Blots were stained with a rabbit polyclonal antibody against the human kainate receptor subunit GluK4 (known as GRIK4 in Genbank) (Chemicon AB5649). Detection was performed with a goat anti-rabbit IgG HRP and chemiluminescence was performed with SuperSignal West Pico Chemiluminescence Substrate (Pierce). To ensure equal loading, Ponceau S (Sigma) staining was performed.

Cell Surface Phenotyping.

All cells were tested for cell surface antigen expression by direct immunofluorescence and flow cytometric analysis. Briefly, 1×106 cells were stained in 100 µl volumes with rabbit anti-human GluK4 (Chemicon) for primary incubation for 30 min at 4° C. After washing, cells were then stained with a PE labeled goat anti-rabbit IgG (BD Pharmingen San Diego, Calif.). After 30 min/4° C. and washing, the cells were examined using a Cytomics FC500 Flow Cytometer and data was analyzed using CXP software (Beckman Coulter Fullerton, Calif.). PI was used to exclude dead cells from the analysis.

Soluble CD23 Release Assay.

For these studies, the CD23+ human B cell line RPMI8866 was grown in the presence or absence of 5 mM KA or Glu for 24 hours in CDMEM10 at a concentration of 1×10$^6$ cells/mL. For antagonist studies, prior to the addition of KA or Glu cells were pre-treated with 50 µM vehicle (DMSO), NBQX, NS 102, or TPM for one hour. After incubation, cell free supernatants were harvested and sCD23 levels determined by ELISA. When primary cells were assayed, cells were cultured with 10 ng/mL IL-4, 1 µg/mL anti-CD40, and 200 ng/mL Il-21 in complete culture media in the presence or absence of 5 mM glutamate. Forty-eight hours later cell free supernatants were harvested for ELISA.

Culture Conditions for Immunoglobulin Analysis.

Primary B cells or PBMC were cultured in the presence of 10 ng/mL IL-4 and 1 µg/mL anti-CD40 in complete culture media in the presence or absence of 5 mM KA or 5 mM Glu. When indicated, 200 ng/mL IL-21 was also added. For antagonism studies, prior to culture primary cells were treated with 10 µM vehicle (DMSO), NBQX, NS102, or TPM. After 14 days of culture, cell free supernatants were analyzed via ELISA for Ig levels. As cells are grown at various densities, line graphs represent Ig production as compared to cell density. When expressed as a bar graph, data represents the cell concentration in which maximum Ig production was observed for the particular isotype displayed.

To determine the effect of ADAM10 inhibition on Ig production, purified human B cells were cultured with 10 ng/mL IL-4, 1 µg/mL anti-CD40, and 200 ng/mL IL-21 in complete culture media in the presence of DMSO as vehicle control or 10 μM ADAM10 specific inhibitor. Five days later, cell free supernatants were harvested for soluble CD23 release and fourteen days later, cell free supernatants were analyzed for Ig production. ELISAs. Human sCD23 ELISA was measured using a standard sandwich ELISA approach, using a mouse anti-CD23 (Clone BU38) coating antibody and sheep anti-CD23 (both from The Binding Site Birmingham, UK). Detection is performed with a goat anti-sheep IgG tagged with HRP (Southern Biotech Birmingham, Ala.). Determination of human IgE levels utilized a monoclonal mouse anti-human IgE antibody (clone 4.15) as a capture. Samples and standards were detected using a rabbit anti-human IgE-HRP (Southern Biotech) diluted in PBS/10% FBS. Human IgG or IgM were detected using a goat anti-human IgG or IgM followed by detection with a goat anti-human IgG or IgM tagged with HRP (All from Southern Biotech). Standards for the IgG and IgM ELISAs were purchased from Sigma. IgE standards were purified from JW8 hybridoma cells as previously described (Caven et al., 2005a). All assays utilized TMB substrate (BD Pharmingen San Diego, Calif.) and the reactions were stopped with 0.18M $H_2SO_4$. Plates are read at a wavelength of 450 nm on a SpectraMax 250 and data analyzed using SOFTmax PRO 3.1.2 software (Molecular Devices, Los Angeles, Calif.).

Proliferation Assay.

Primary B cells were cultured with 10 ng/mL IL-4, 1 μg/mL anti-CD40, and 200 ng/mL IL-21 in CDMEM-10 in the presence or absence of 5 mM glutamate at a concentration of 150,000 cells/well in sterile 96-well culture plates. When PBMC is used the cell concentration is 100,000 cells/well. Prior to the addition of glutamate, cells were pretreated for 1 hour with 10 μM vehicle (DMSO) or NS102. After 96 hours of growth, a 24 hr pulse $[H^3]$-thymidine (Perkin Elmer) was used. Plates were then harvested using a Filtermate cell harvester onto GFC plates. Assays were read using a Topcount Plate Counter (Perkin Elmer, Waltham, Mass.).

Analysis of Cell Division.

Carboxyfluorescein diacetate succinimidyl ester (USE) (Molecular Probes Eugene, Oreg.) was prepared according to the manufacturer's recommendations. Resting B cells were washed and re-suspended at $5 \times 10^6$ cells/mL in PBS. CFSE was then added at the manufacturer's recommended dilution and incubated in the dark at room temp for 5 minutes. Reaction was quenched by the addition of ice cold FBS and cells were then washed and plated at $1 \times 10^4$ cells/200 μl in a 96 well plate containing 10 ng/mL IL-4, 1 μg/mL anti-CD40, and 200 ng/mL IL-21 in the presence or absence of glutamate. After 5 days of culture, cells were harvested and analyzed by flow cytometry using a BD Canto. Analysis was performed using FCS Express software V3.

Data Analysis.

Data are summarized as mean±Standard error (SE). The statistical analysis of the results was performed by the student's t test. A p-value of <0.05 was considered significant. When primary cells are used, data is one representative donor but all assays have been performed using a minimum of three donors with similar results.

Results

Kainate Receptors are Present on Human B Cells

Figure 1B:
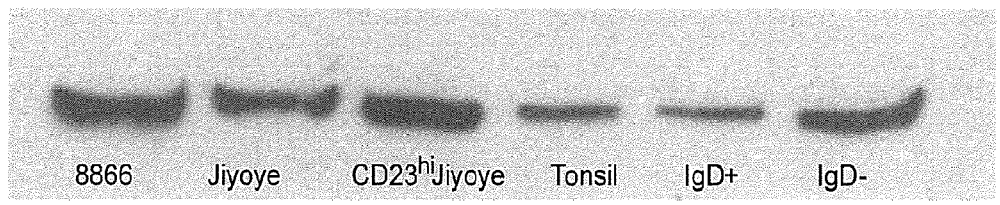
Figure 1C:
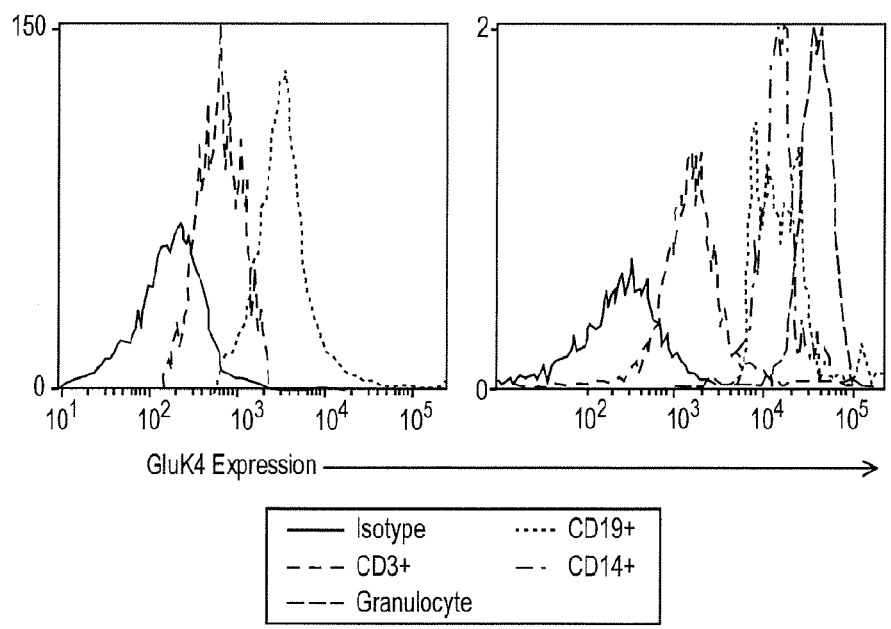

KARs are multi-subunit receptors consisting of four distinct subunits. The gene names for these subunit are designated as GRIK1-5, whereas the protein names are GluK1, GluK2, GluK3, GluK4, and GluK5 (Collingridge et al. 2009). Thus, to form a functional receptor, KARs must consist of GluK1 or GluK2 in combination with GluK3, GluK4, and GluK5. Two of the genes that encode subunit GluK1 (GRIK1) and GluK2 (GRIK2), can undergo specific RNA editing and thus result in two transcript variants (TVs). From the data shown, we observe the presence of four subunit gene products, GRIK2, GRIK3, GRIK4, and GRIK5, thus, it is evident that message for KARs do exist in human B cells (FIG. 1A). It appears that the immune type of kainate receptor is the GluK2 (GRIK2) containing receptor as evidenced by the presence of this transcript. Furthermore, the fact that four subunits are present would indicate the potential presence of a functionally active receptor. We confirmed our RT-PCR data by showing protein expression of the kainate receptor subunit GluK4 (GRIK4) by Western Blot analysis, using B cell lines and primary human lymphocytes (FIG. 1B). We focused on the presence of GluK4 (GRIK4) as it is required for ligand binding. In addition, flow cytometric analysis confirmed that KARs are cell surface expressed on both RPMI8866 (data not shown) and primary human leukocytes from PBMC and tonsils (FIG. 1C).

KAR Activation Increases ADAM10 mRNA and Activity

Figure 2A:
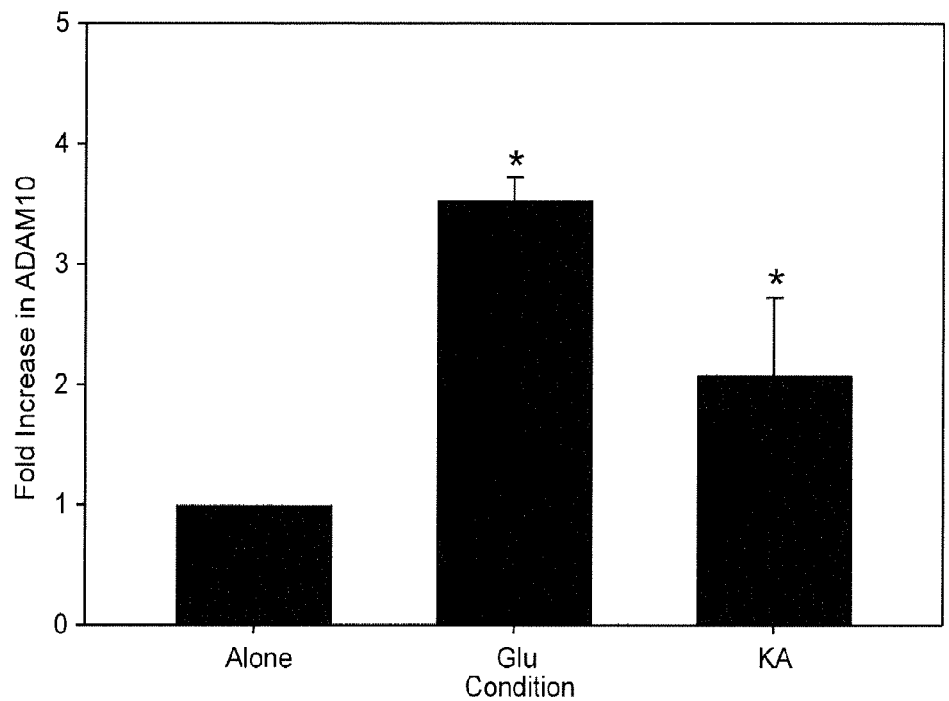
FIG. 2A-D. Kainate receptor activation increases ADAM10 levels. (A) Primary B cells were cultured in CDMEM-10 alone, 5 mM glutamate, or 5 mM kainic acid for 30 minutes. RNA was then isolated and subjected to qPCR analysis as described. Levels are normalized to human betaactin. Shown is the average of three separate donors. (B) Soluble CD23 release is also increased post KAR activation in RPMI8866 cells and primary human B cells (C). Sum of four individual donors; data is graphed as fold increase to normalize data to account for individual variance. (D) RPMI8866 cells were pretreated with either vehicle control (DMSO), a AMPAR antagonist (NBQX), a NMDAR antagonist (TPM), or a KAR antagonist (NS 102) (50 μM) for one hour prior to the addition of 5 mM glutamate or 5 mM KA. 24 hours later, soluble CD23 levels were determined as described. Shown is the average+/−SE of three individual experiments. *Significant at p<0.05; NS—not significant FIG. 3A-D. Kainate receptor activation increases IgE synthesis. Primary B cells were cultured in the presence of 10 ng/mL IL-4 and 1 μg/mL anti-CD40 in CRPMI-10 in the presence or absence of (A) 5 mM KA or (B) 5 mM Glu. After 14 days of culture, cell free supernatants were analyzed via ELISA for IgE levels. (C) Primary B cells were cultured in the presence of IL-4 and anti-CD40 as in (A) plus 200 ng/mL IL-21 in the presence or absence of 5 mM glutamate in CDMEM-10. After 14 days of culture, cell free supernatants were analyzed via ELISA for IgE levels. (D) Before culture primary B cells were treated with 10 μM vehicle (DMSO), NBQX, or NS102. Primary B cells were then cultured in similar conditions as in C. After 14 days, ELISA analysis was performed. Part A, B, and C represent three different individuals that serve as a representative donor. Part D is the cell concentration in which maximum Ig production was observed (9,000 cells/well) either in the presence or absence of antagonist from another donor. Both the RPMI and DMEM culture experiments have been performed a minimum of three times with similar results. * indicated p<0.05 as compared to indicated control. # indicates p<0.01 as compared to indicated control.
Figure 2B:
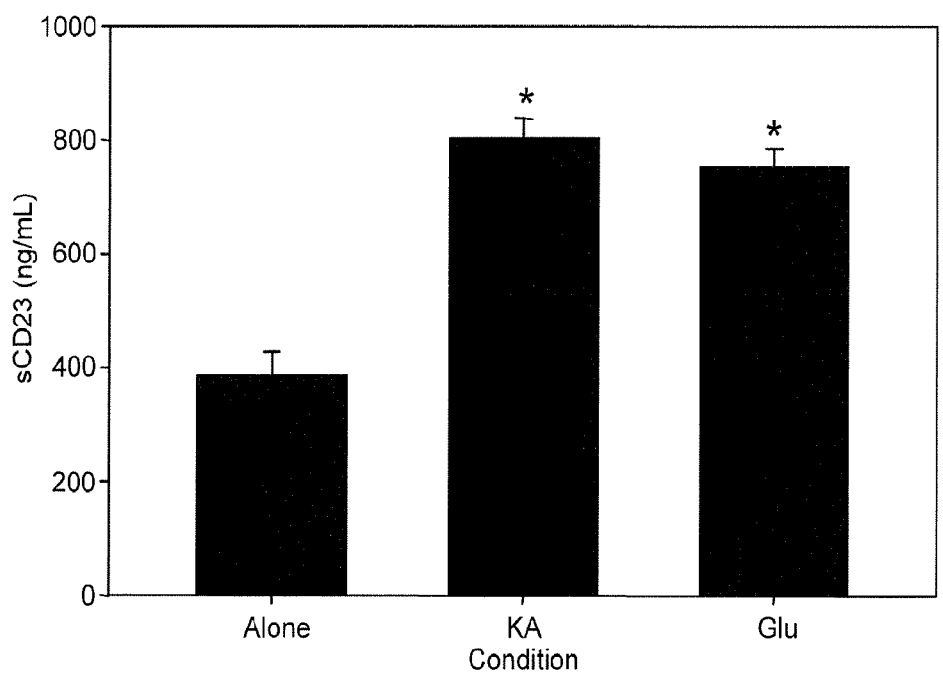
Figure 2C:
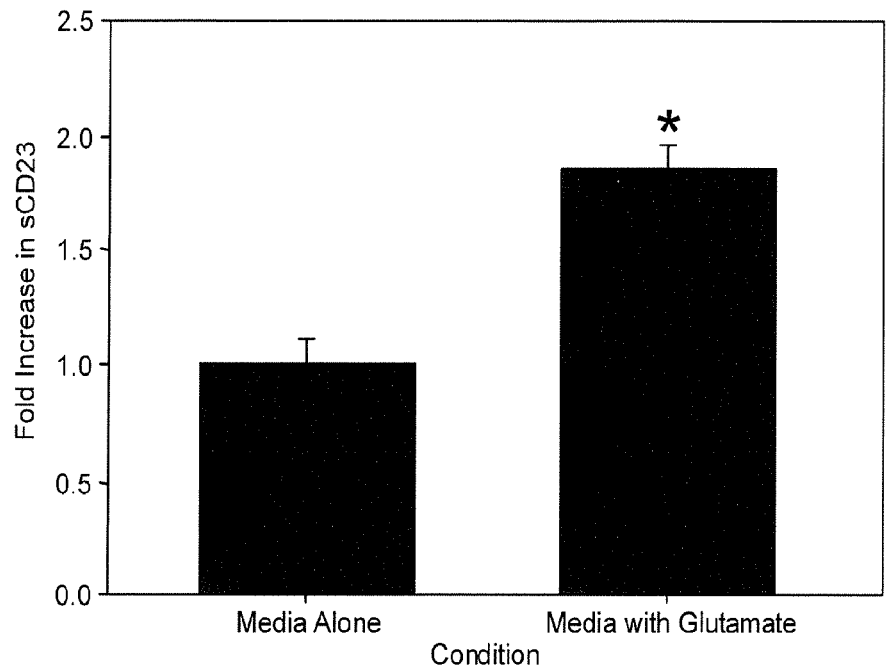

Based upon the publication by Ortiz et al., KAR stimulation in the CNS led to an increase in ADAM10 mRNA. In order to determine if kainic acid (KA), an exogenous ligand, or glutamate (Glu), an endogenous ligand, has the ability to increase ADAM10 message levels in the human immune system, purified human B cells were cultured in the presence of KA or Glu for 30 minutes and then RNA analyzed by qPCR for ADAM10 expression. As evidenced in FIG. 2A, there is a significant increase in the mRNA levels for ADAM10 after KAR activation in primary B cells. In keeping with ADAM10's newly identified role as the CD23 sheddase, it was anticipated that KAR activation would increase soluble CD23 release. For these studies, the CD23+ human B cell line RPMI8866 was utilized and experiment was performed as outlined in Materials and Methods. As shown in FIG. 2B, a significant elevation in the amount of sCD23 released is seen following KAR activation by either KA or glutamate. We also wanted to determine if this same increase in sCD23 release is observed in primary human B cells. B cells were cultured in the presence of IL-4, anti-CD40, IL-21, +/−5 mM glutamate for 48 hours. The reason that primary cells are cultured longer than RPMI8866 is that CD23 first needs to be upregulated, which takes approximately 24 hours, before it can be cleaved. FIG. 2C shows that sCD23 release is also appreciably increased in primary human B cells in the presence of glutamate.

Figure 2D:
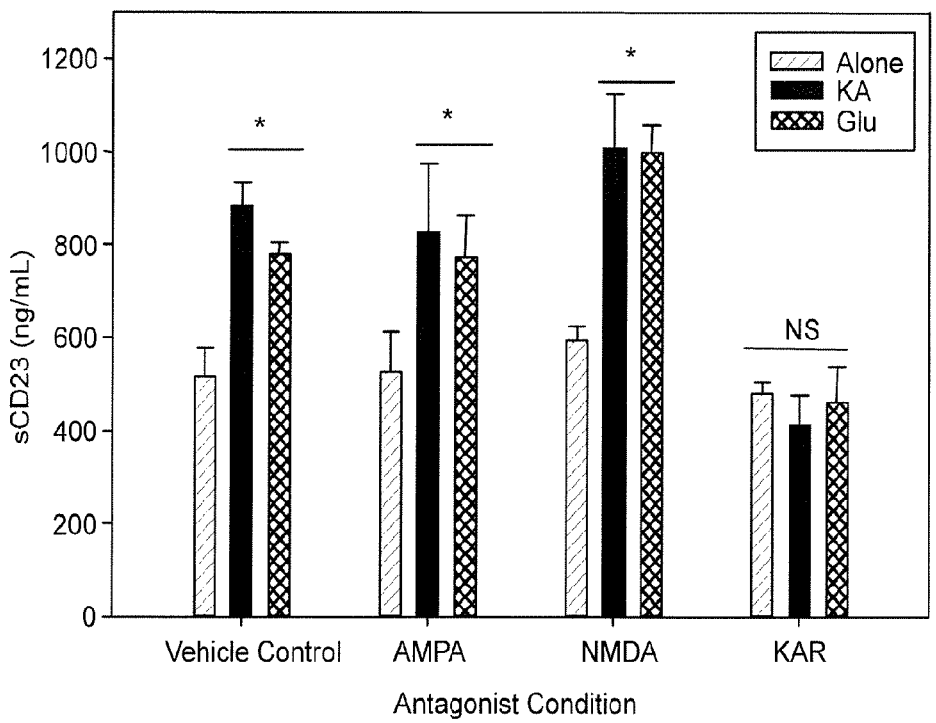

As stated earlier, three types of ionotropic glutamate receptors, NMDAR, AMPAR, and KAR exist. High doses of kainic acid can activate AMPA receptors and both AMPA and NMDA receptors have been described on other immune cells (Lerma et al., 2001; Ganor et al., 2003b), (Boldyrev et al., 2005). Therefore, receptor antagonists were used to confirm that the KAR was indeed responsible for the enhanced CD23 cleavage. NS102 is a specific KAR antagonist (Du et al., 2009; Verdoorn et al., 1994), NBQX is antagonist of the AMPA receptor (Hou et al., 2009) and topiramate (TPM) is a NMDA antagonist (Rawls et al., 2009). The soluble CD23 release assays were performed as before, except the RPMI8866 cells were incubated with 50 μM of the antagonist for 1 hr prior to the addition of KA or Glu. FIG. 2D shows that none of the antagonists have any effect on baseline sCD23 release. Furthermore, only NS 102, the KAR specific antagonist, could prevent the significant increase observed in the presence of KAR stimulation. Verdoom et al. showed that NS102 selectively antagonizes GluK2 containing KARs (Verdoorn et al., 1994). This fact is in agreement with our data in that we observe the GluK2 subtype of the KAR receptor in the immune system and indeed NS 102 does block. This shows that this phenomenon is KAR specific due to the fact that no change is observed in the presence of the AMPAR or NMDAR antagonists. Thus, the observations made are a direct result of KAR activation on the human B cells.

KAR Activation Increases IgE Synthesis

Figure 3A:
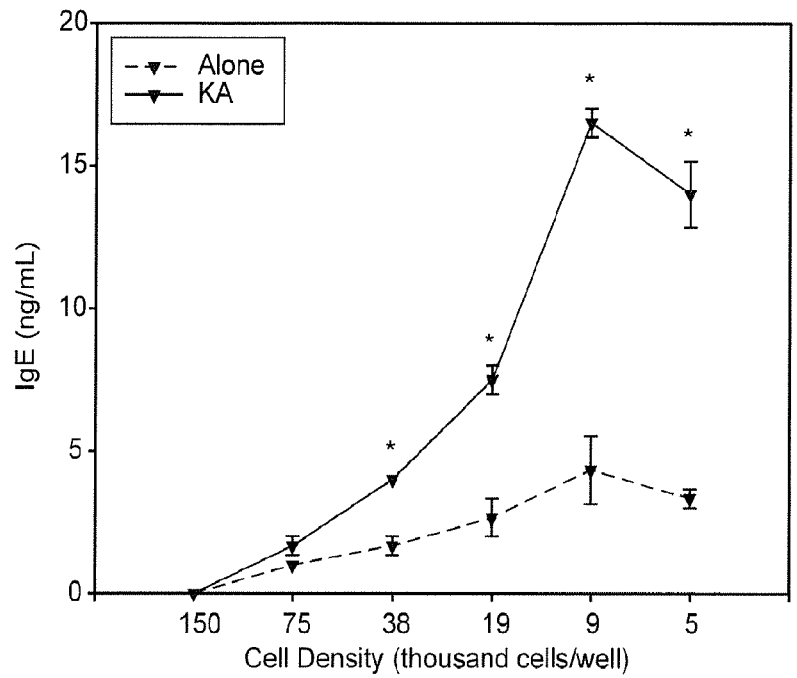
Figure 3B:
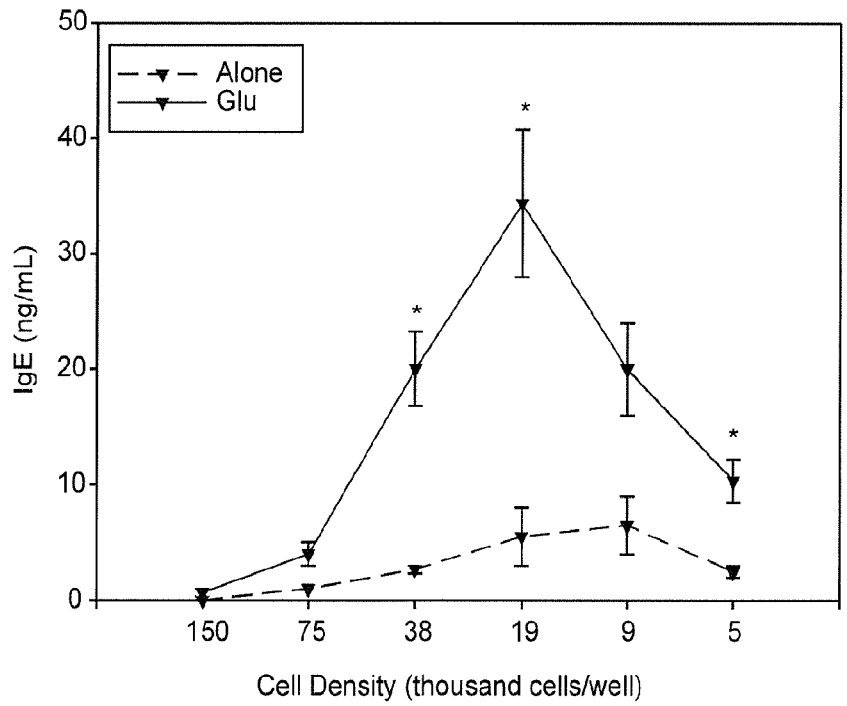

Because there was a significant increase in sCD23 released from the cell surface, the natural extension of these studies was to look at IgE synthesis as CD23 is a regulator of IgE production. Primary human B cells were stimulated with IL-4 and anti-CD40 to stimulate IgE production and cultured in the presence or absence of KA. When KA is present in the media, there is a strong and statistically significant increase in the amount of IgE produced (FIG. 3A). The cultures were performed at multiple cell concentrations as our laboratory has previously reported that cell density inversely correlates with IgE production (Rabah and Conrad, 2002), (Caven et al., 2005b). To determine physiological relevance, the studies were repeated with the natural ligand glutamate. A similar increase in the amount of IgE synthesized from purified human B cells in the presence of glutamate (FIG. 3B) was seen. Thus, we chose to utilize the natural ligand for the remainder of the studies.

Figure 3C:
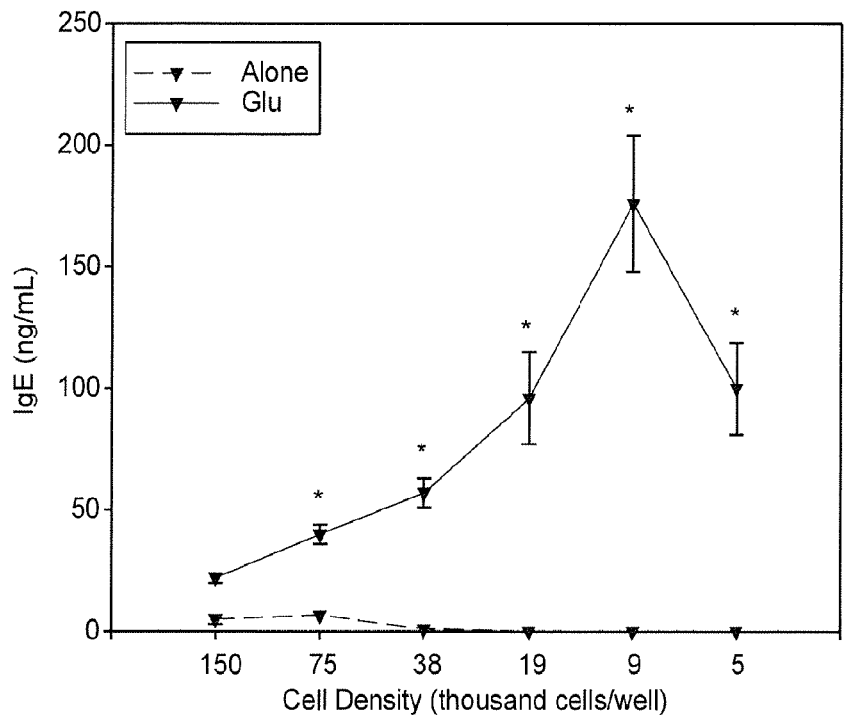

Our laboratory has previously shown that the addition of IL-21 can enhance IgE production in the human system (Caven et al., 2007) due to the fact that IL-21 augments plasma cell development in human in vitro cultures. Thus, IL-21 was added into our culture system to determine if the glutamate mediated effect on IgE synthesis was still seen even in the presence of the additional cytokine stimuli. This effect is illustrated by the fact that cultures with IL-21 and glutamate make much more IgE than either IL-21 alone or with glutamate alone as indicated by the scale on the y axis of the ELISA graphs (FIG. 3C).

RPMI-1640, the primary media most utilized for lymphocyte culture, contains 0.1 mM glutamate. To better control for and determine the actual role of the glutamate mediated increase in IgE, we switched these studies to using DMEM based media, which lacks any glutamate. In the DMEM based media we observed a pronounced increase in the amount of IgE generated in the presence of glutamate and IL-21(FIG. 3C). Thus all remaining studies will employ the use of DMEM based media with the addition of IL-21.

Figure 3D:
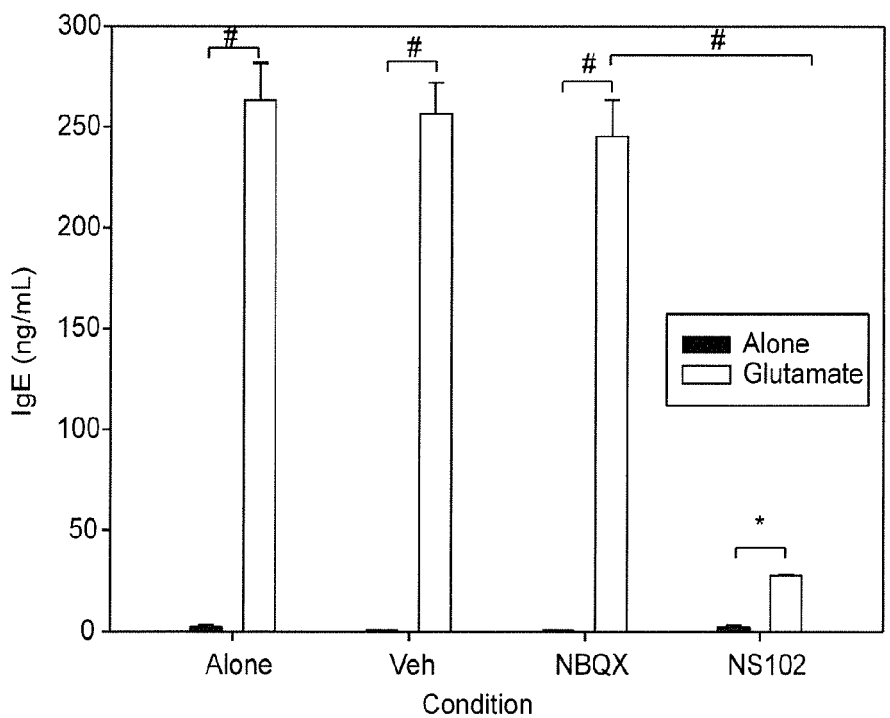

To confirm that the glutamate mediated increase in IgE is mediated through the kainate receptor, the antagonists used in the soluble CD23 studies were employed. As evidenced in FIG. 3D, we see no effect with either vehicle (DMSO) or the AMPA antagonist, NBQX. However the KAR antagonist, NS102, almost completely blocks the glutamate mediated increase in IgE production. While the IgE production in wells containing both Glu and NS-102 is still significantly higher than the control wells lacking Glu the amount of IgE produced is dramatically reduced (p<0.00001) when compared to Glu containing cultures. In separate experiments, TPM also did not influence IgE production (data not shown), further confirming the KAR specificity.

KAR Activation Leads to an Increase in Cell Proliferation

Figure 4A:
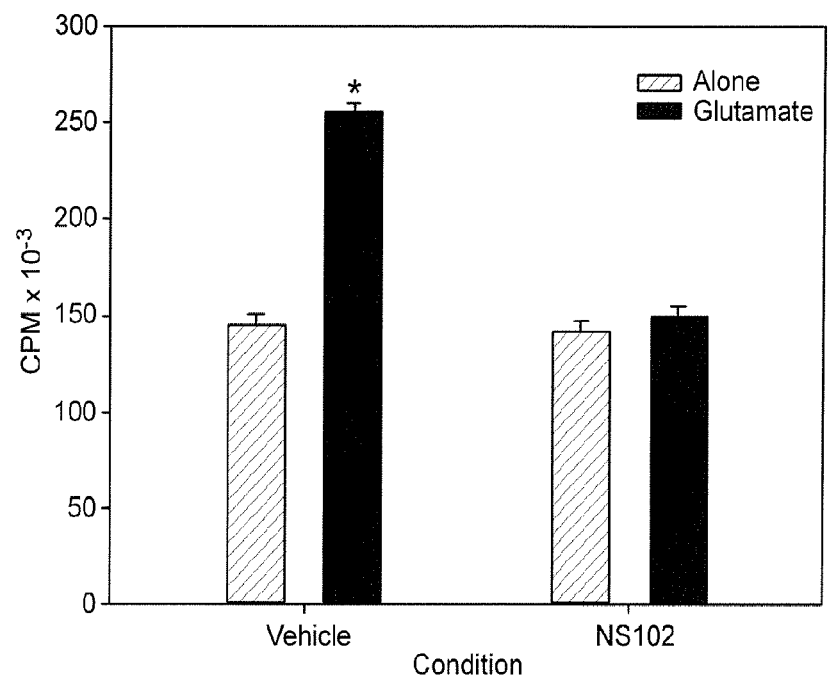
FIGS. 4A and B. Kainate receptor activation increases cellular proliferation. (A) Primary B cells were cultured as in FIG. 3C in CDMEM-10 in the presence or absence of 5 mM glutamate at a concentration of 150,000 cells/well. Prior to the addition of glutamate, cells were pretreated for 1 hour with 10 μM vehicle (DMSO) or NS102. After 96 hours, cells were pulsed for 24 hrs with [³H]-thymidine. Shown is one representative donor of three performed. * indicates p<0.05 as compared to vehicle alone. (B) Primary B cells (104/well) were labeled with CFSE as indicated in Materials and Methods and were cultured with IL-4, anti-CD40, IL-21 in CDMEM-10 alone (-) or in the presence of 5 mM glutamate (-•-•-). CFSE fluorescence was determined on day 5 post culture initiation. Part B representative of two of similar design.
Figure 4B:
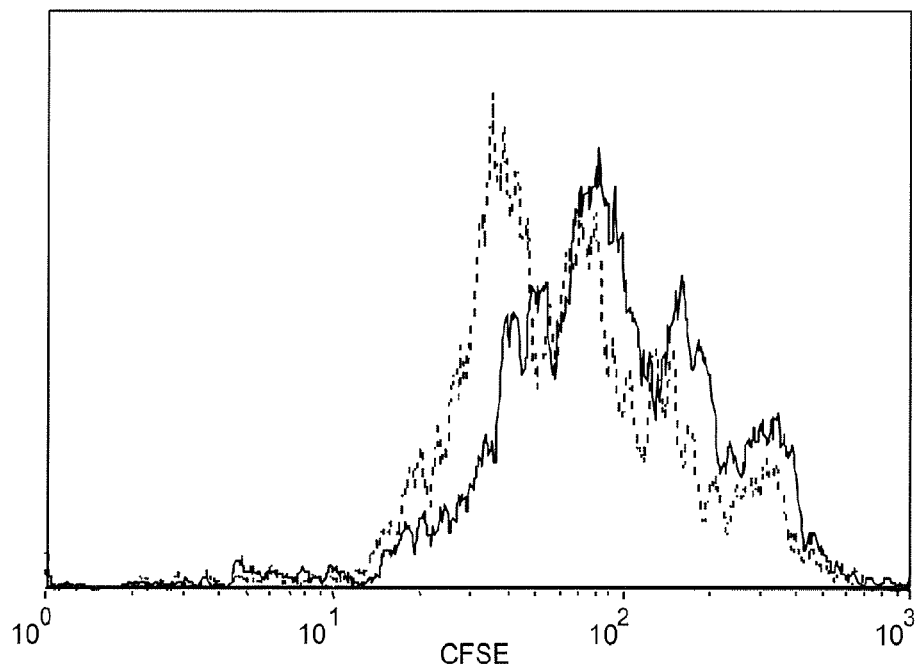

B cells were cultured in the presence or absence of Glu to examine changes in proliferation. Our laboratory has previously confirmed that B cell proliferation and human IgE synthesis are correlated and increased in the presence of IL-21. In order to examine if this phenomenon held true in the presence of KAR agonism, primary human B cells were grown in the presence/absence of glutamate and cell proliferation was determined. From the data shown, KAR activation leads to a significant increase in proliferation (FIG. 4) which is prevented in the presence of NS 102. Taken together, our data coupled with previous data shown by other groups indicating the need for a proliferative response required for IgE synthesis clearly strengthens the argument that KAR activation via glutamate signaling can promote an enhanced humoral response and the enhanced IgE production would be anticipated to enhance an atopic phenotype.

KAR Activation Increases IgG Synthesis

Figure 5A:
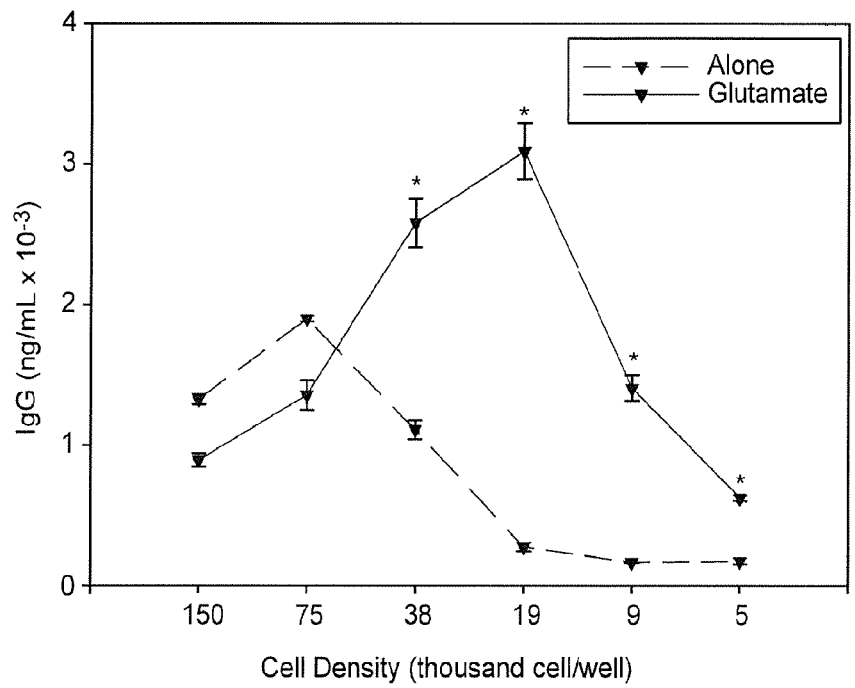
FIG. 5A-C. Kainate receptor activation increases total IgG synthesis. Primary B cells were cultured as in FIG. 3C in CDMEM-10 in the presence or absence of 5 mM glutamate. After 14 days of culture, cell free supernatants were analyzed via ELISA for (A) IgG levels or (C) IgM levels. (B) Before culture primary B cells were treated with 10 μM vehicle (DMSO), NBQX, or NS102. Primary B cells were then cultured in similar conditions as in (A). After 14 days, ELISA analysis performed. Shown in B is one cell concentration with highest Ig production (38,000 cells/well). Each panel is one representative donor. Experiment shown is one of three with similar outcomes. * indicated p<0.05 as compared to alone. # indicates p<0.01 as compared to indicated control. NS—not significant.
Figure 5B:
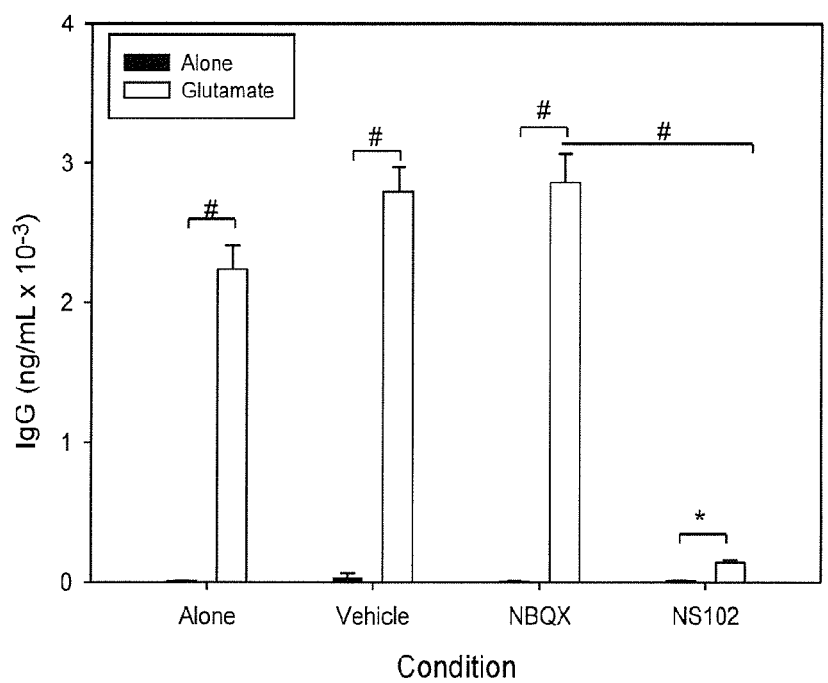
Figure 5C:
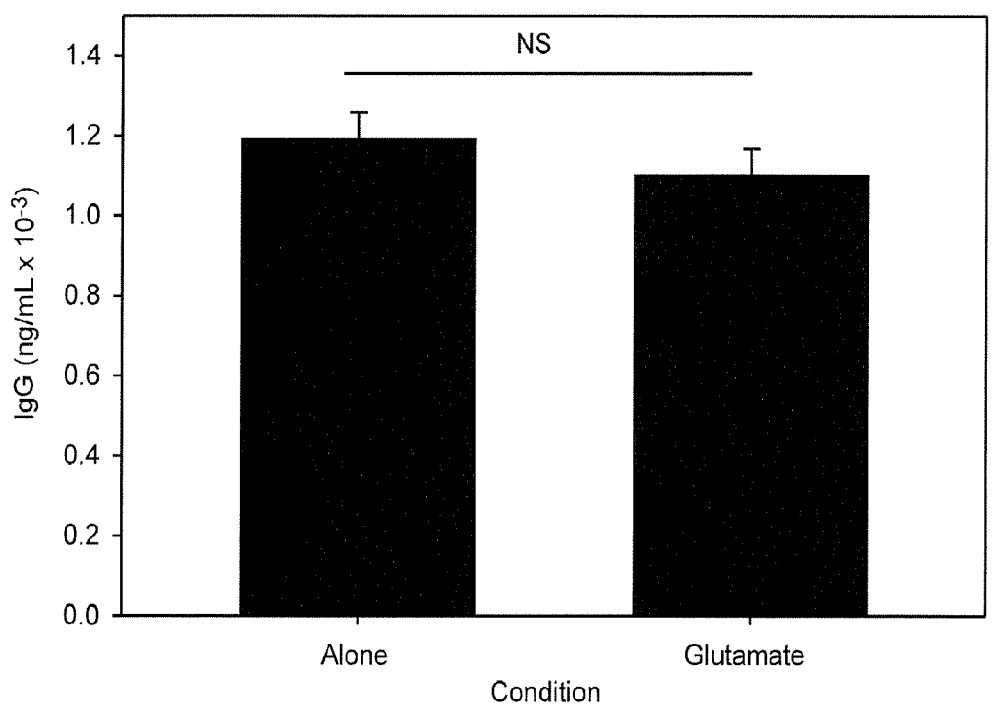

To determine if glutamate stimulation through the KAR would enhance other immunoglobulin isotypes, we examined total IgG and 101 secretion from B cell cultures. A similar phenomenon in terms of IgG production was observed as compared to the glutamate mediated IgE enhancement. Enhancement in IgG production was seen in all but the highest density cultures (FIG. 5A). This enhancement was blocked by the KAR antagonist, NS102, but was unaffected by either vehicle control or the AMPA antagonist, NBQX (FIG. 5B). However, total IgM levels were not influenced. The IgM data is shown at a single concentration (150,000 cells/well) but no enhancement of IgM was seen at any cell concentration (FIG. 5C).

Glutamate Enhancement is Also Seen in PBMC Cultures.

Figure 6A:
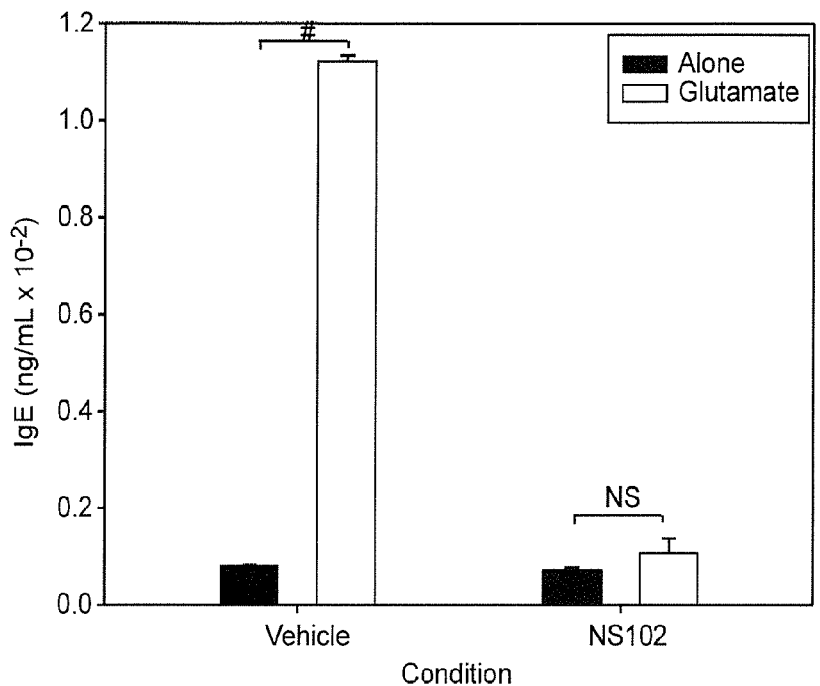
FIG. 6A-D. Kainate receptor activation in human PBMC model. Human PBMC were cultured in the presence of 10 ng/mL IL-4, 1 μg/mL anti-CD40, and 200 ng/mL IL-21 in CDMEM-10. Prior to the addition of glutamate, cells were pretreated for 1 hour with 10 μM vehicle (DMSO) or NS102. After 14 days of culture, cell free supernatants were analyzed for IgE (A), total IgG (B), or IgM (C). The cell concentration showing maximum Ig production is shown in the presence or absence of Glu. These cell concentration values were 18,000 cells/well (A), 38,000 cells/well (B) and 300,000 cells/well (C). Separate, identical cultures (150 K/well) were plated to analyze cellular proliferation (D). Shown in each is one representative donor. A total of 3 PBMC cultures have been examined in this manner with similar results. * indicated p<0.05 as compared to alone. # indicates p<0.01 as compared to indicated control. NS—not significant.
Figure 6B:
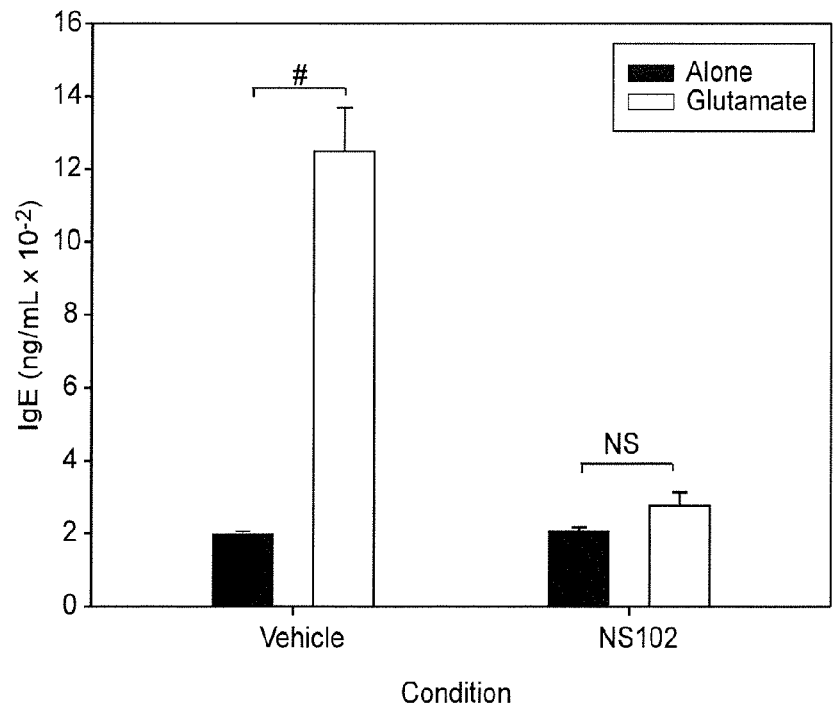
Figure 6C:
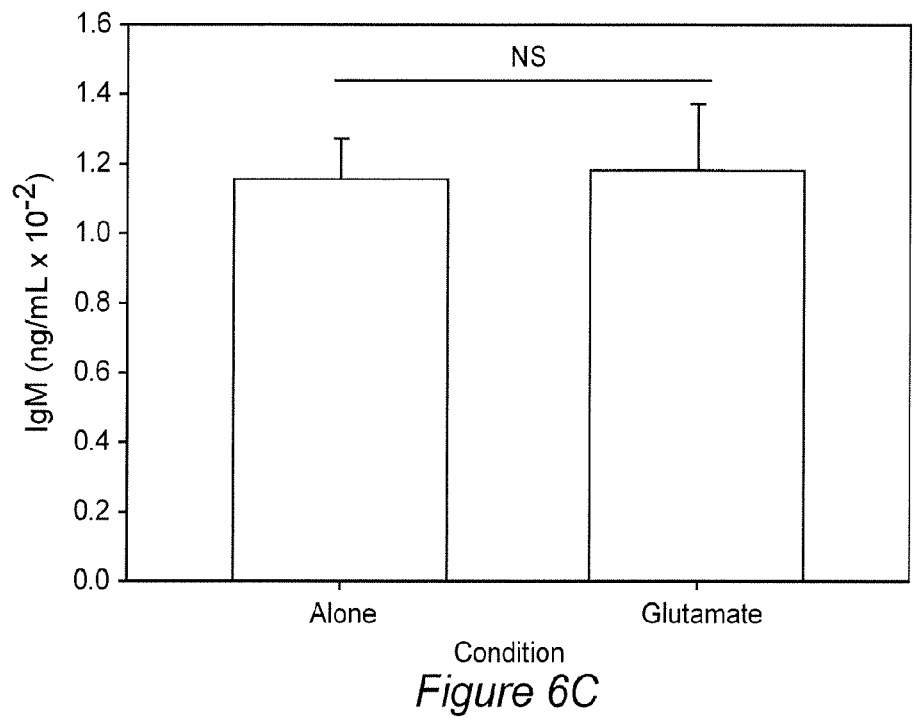
Figure 6D:
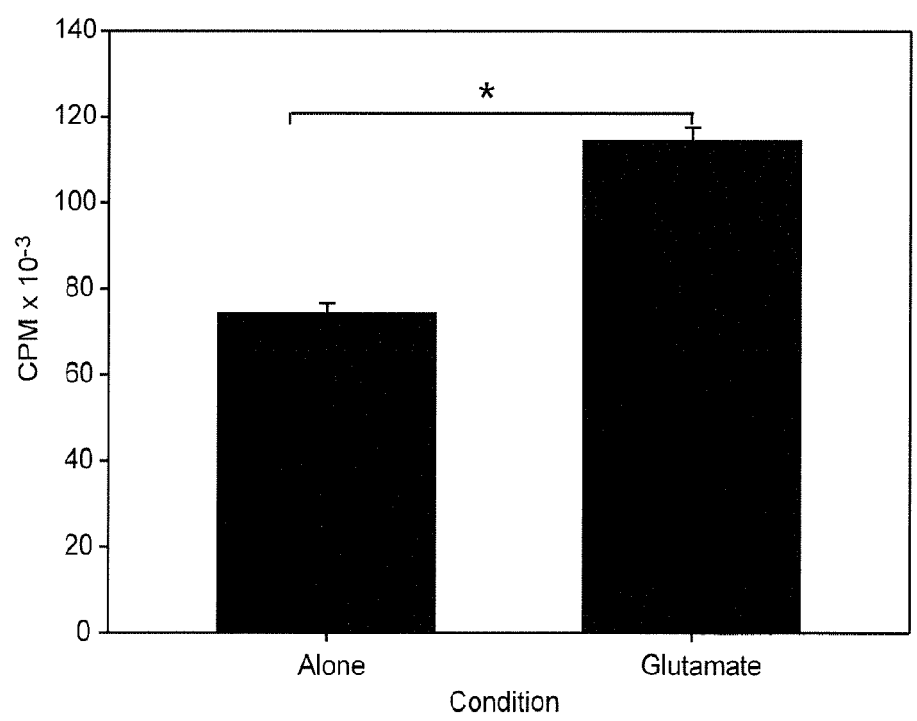

The aforementioned studies used purified B cells. In order to determine if the enhancement was still effective with the cellular milieu that closely mimics the immune system, we examined effect of KAR agonists on IgE production using PBMC. As can be seen in FIG. 6A, addition of glutamate to the PBMC cultures that are stimulated with anti-CD40, IL-4, and IL-21 again resulted in a very strong enhancement of IgE synthesis. Other immunoglobulins (total IgG and IgM) were also tested and while IgG enhancement was seen (FIG. 6B), IgM production in the PBMC cultures, as with purified B cells, was not significantly influenced (FIG. 6C). The KAR specific antagonist, NS-102, again strongly blocked the increase in IgE and IgG production. Note that the cell concentrations used for the NS 102 were where maximum Ig production was seen. In a similar fashion as with purified B cells, proliferation was also affected by the addition of glutamate (FIG. 6D).

Glutamate Enhancement of sCD23 and Ig Production is ADAM10 Dependent

Figure 7A:
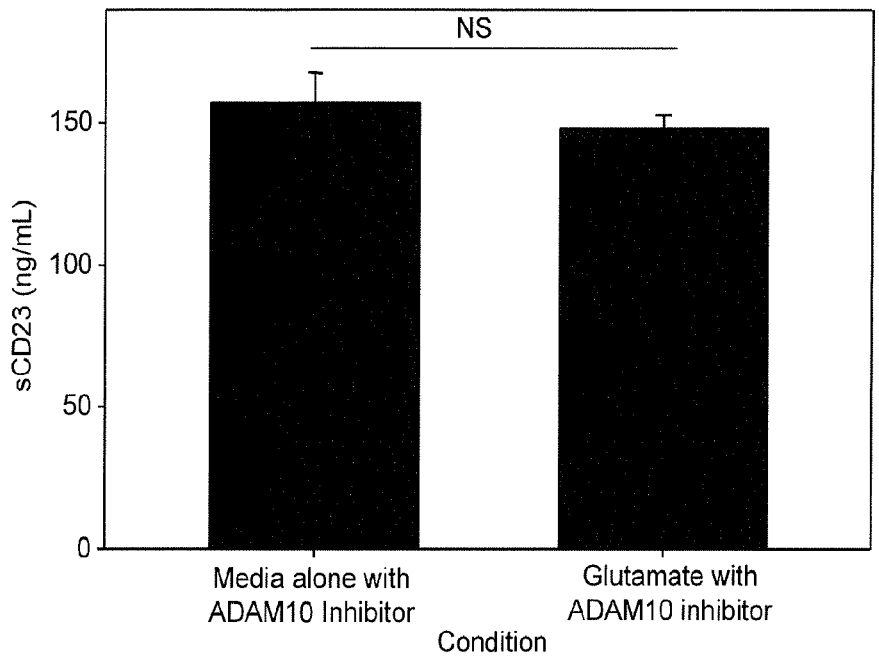
FIGS. 7A and B. Glutamate enhancement of sCD23 and Ig production is ADAM10 Dependent (A) RPMI8866 cells were treated with 10 μM ADAM 10 inhibitor or vehicle control prior to the addition of 5 mM glutamate. 24 hours later cell free supernatants were harvested for sCD23 release. (B) Primary human B cells were cultured with 10 ng/mL IL-4, 1 μg/mL a-CD40, and 200 ng/mL IL-21 in the presence of 10 μM ADAM10 inhibitor or vehicle control. Cell free supernatants were analyzed for either sCD23 on day 5 or Ig production by ELISA on day 14 as described. Shown is data summary for five donors. Data is normalized and shown as percent inhibition.

Ortiz et al. originally reported that KAR activation increased ADAMs other than ADAM10 and KAR activation has been linked to the increase in several other matrix metalloproteinases (Szklarczyk et al., 2002; Flood et al., 2007). Hence we next wanted to determine if the KAR mediated increase in sCD23 was due to ADAM10 activation. Prior to the addition of glutamate, RPMI8866 were incubated with 10 μM ADAM10 specific inhibitor. FIG. 7A shows that glutamate cannot overcome the ADAM10 mediated inhibition of sCD23 further indicating that the increase in sCD23 observed in the presence of glutamate is mediated through a KAR specific activation of ADAM10.

Figure 7B:
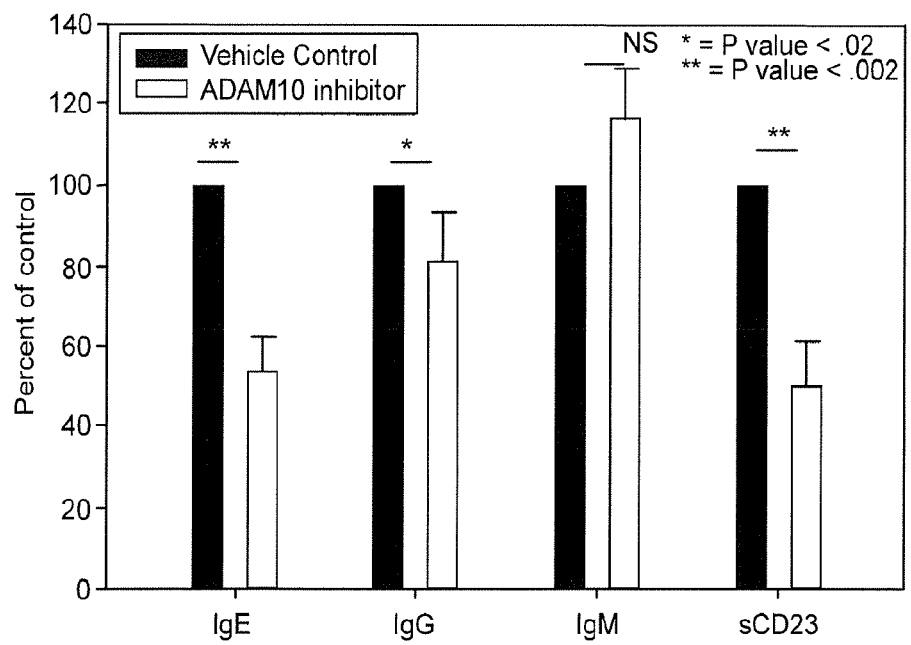

While ADAM10 is appreciated to be the CD23 sheddase, the effects of ADAM10 on immunoglobulin production have not been directly examined. Primary human B cells were treated with an inhibitor of ADAM10 to determine the effects of ADAM10 inhibition on human immunoglobulin production. From the data presented in FIG. 7B, it is evident that ADAM10 inhibition blocks CD23 shedding as expected as well as IgE and IgG production; however no effect was seen on IgM. Interestingly this data inversely correlates with our KAR studies in that ADAM10 increases lead to an increase in sCD23, IgE, and IgG with no effect on IgM. Thus we have shown that ADAM10 modulation does indeed impact B cell Ig production.

Discussion

This study shows that a functional glutamate receptor of the kainate subtype exists in the human immune system.

While there are studies to date which report that glutamate receptors exist on human T cells (Ganor et al., 2003a) and macrophages (Boldyrev et al., 2004), their presence has not been demonstrated on B cells. While those studies are important in illustrating that glutamate receptors do exist in the immune system, our study is pivotal in that receptors of the kainate subtype to our knowledge have never been reported to exist in lymphocytes. The only other KAR demonstration in the hematopoietic system was the very recent finding that KARs are on platelets, and stimulation thereof promoted cyclooxygenase activation (Sun et al., 2009).

Aside from the presence of the receptors themselves functional relevance was also shown. In view of the recent demonstration that ADAM10 is the primary CD23 sheddase, we searched for agents that would modify ADAM10 activity. The overall purpose was to test the hypothesis that ADAM10 modulation would, by virtue being the CD23 sheddase, result in IgE modulation. This hypothesis was confirmed. Normal CD23 cleavage was found using both ADAM9 and ADAM15KO mice, thus, up-regulation of ADAM10 is responsible for the observed changes in the CD23. Furthermore, the use of the ADAM10 specific inhibitors confirms both the importance of ADAM10 in B cell immunoglobulin production as well as specific actions of KAR activation leading to ADAM10 activation.

In addition to its effect on CD23 shedding, KAR activation also leads to a significant increase in cell proliferation. As evidenced by our group as well as others, cellular proliferation is a key element in generating strong class switch recombination as multiple rounds of cell divisions are needed for this to occur (Hasbold et al., 1998). In the human system, it is known that at least eight cell divisions are needed in order to produce IgE (Caven et al., 2005a). Thus, the increase in proliferation may help explain the increased class switching observed as indicated by elevated levels of total IgG and IgE. Note that class switching occurs both in the presence and absence of KAR stimulation and that what is seen is a dramatic increase in the synthesis of class switched Ig. There is precedent for KAR activation to cause increasing cell proliferation as it has been shown in the literature that elevated glutamate levels promote growth of human histiocytic lymphoma cells (Haas et al., 2005), yet the mechanism for this increase was not examined. Increased CD23 cleavage also correlates with elevated IgE production and this may also relate to the results shown here as past studies have highlighted CD23's important role as a negative regulator of IgE synthesis. Given the relatively modest influence on cell divisions (FIG. 4), enhancement in proliferation is not likely to be the complete explanation for the Ig production enhancement. The increased ADAM10 activity results in increased sCD23. This has been shown to correlate with increased IgE production in the mouse system (Ford et al., 2006) as well as the human (Saxon et al., 1990). High membrane CD23 levels, caused by transgene over expression (Payet-Jamroz et al., 2001) resulted in decreased IgE and IgG1 expression, at least in the mouse system. Thus, CD23 alteration may at least provide a partial explanation for the results shown in this study.

As aforementioned, elevated glutamate levels have recently been implicated in a variety of peripheral diseases such as certain cancers, HIV, epilepsy, RA, and SLE and certain treatments for autoimmune disease can also affect glutamate levels. This correlates with the phenomena we observe in vitro in the presence in KAR activation, suggesting that glutamate enhancement of IgG and IgE production plays a role in the disease progression.

The concentration of glutamate used in our studies is likely to be physiologically relevant, based on reports that glutamate concentrations in the brain are as high as 15 mM. In the periphery serum glutamate levels may not reach levels as high as these but they have been reported in the millimolar range. Furthermore, it is appreciated that dendritic cells release glutamate themselves and directly act on T cells in the immunological synapse. Thus it is feasible that the localized concentration of glutamate released to the B cell would be in the ranges used in this study.

This example provides support for developing new therapies for immune disease. Especially intriguing is the strong inhibition of Ig production seen with the KAR antagonist, NS-102. NS102 is an antagonist to the GluK2 containing KARs thus confirming specificity of the KAR subtype observed in the human immune system. As KAR knockouts showed minimal CNS effects (Mulle et al., 1998), NS-102 may represent a new tool to control Ig synthesis. Alternatively, it may be possible to produce related KAR antagonists that are engineered to not cross the blood brain barrier. These antagonists would potentially have no or minimal CNS issues and would thus have the potential to strongly reduce peripheral Ig production and control the IgG and IgE mediated diseases.

Example 2

In order to further confirm that the kainate receptor could play a role in B cell hyperactivity as seen in autoimmunity, KAR knockout mice were obtained and studied. These mice had been engineered by a neomycin disruption of the GRIK2 gene and have been characterized and extensively studied in the CNS field (Mulle et al., 1998). It is important to note that in the absence of this subunit, a functional kainate receptor fails to form. While these mice have been studied in the context of neurological disease, to our knowledge nothing has been reported about the immune systems of these mice.

In initial studies, we confirmed the importance of the KAR receptor in B cell biology by using in vitro analysis. When cultured, B cells from these KAR KO mice did not show any enhanced sCD23 release, proliferation, or Ig synthesis in the presence of glutamate (data not shown).

Figure 8:
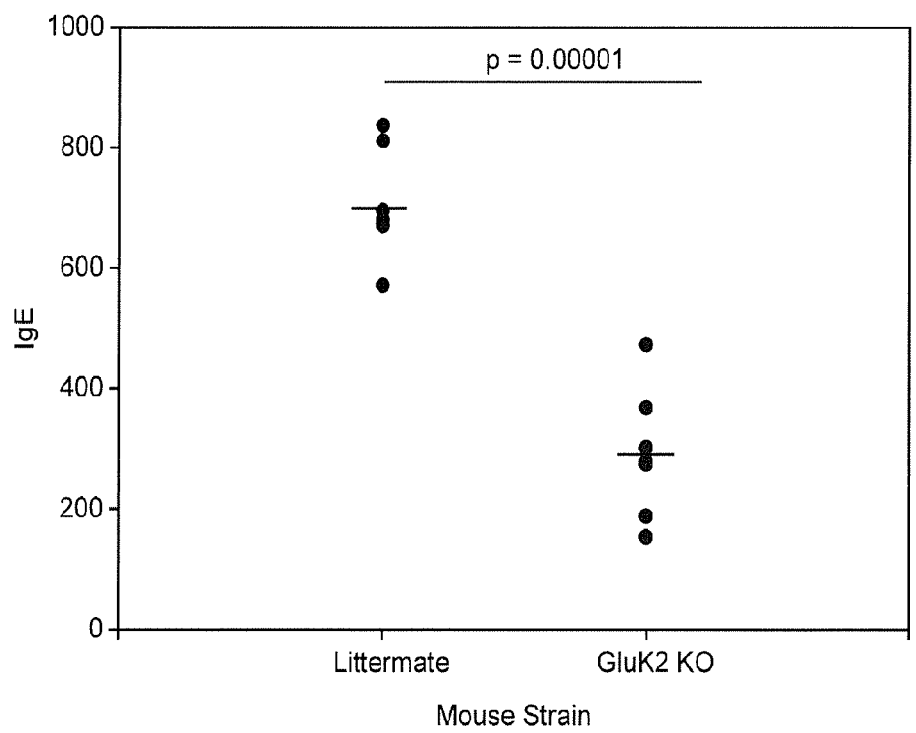
FIG. 8. Comparison of KAR knockout mice to wild type mice after antigen challenge according to an accepted experimental model of allergic disease.

We next compared the responses of KAR knockout mice to wild type mice after antigen challenge using an accepted experimental model of allergic disease. Wild type and KAR knockout (KO) mice were given ovalbumin (Ova) in alum on day 0, and 14 days later the mice were boosted. On day 21, mice were sacrificed by cardiac puncture and IgE levels were analyzed by ELISA. The results are presented in FIG. 8. As can be seen, there is clearly a reduction in the amount of IgE produced after antigen challenge in the absence of the kainate receptor (i.e. in the KAR KO mice).

Figure 9:
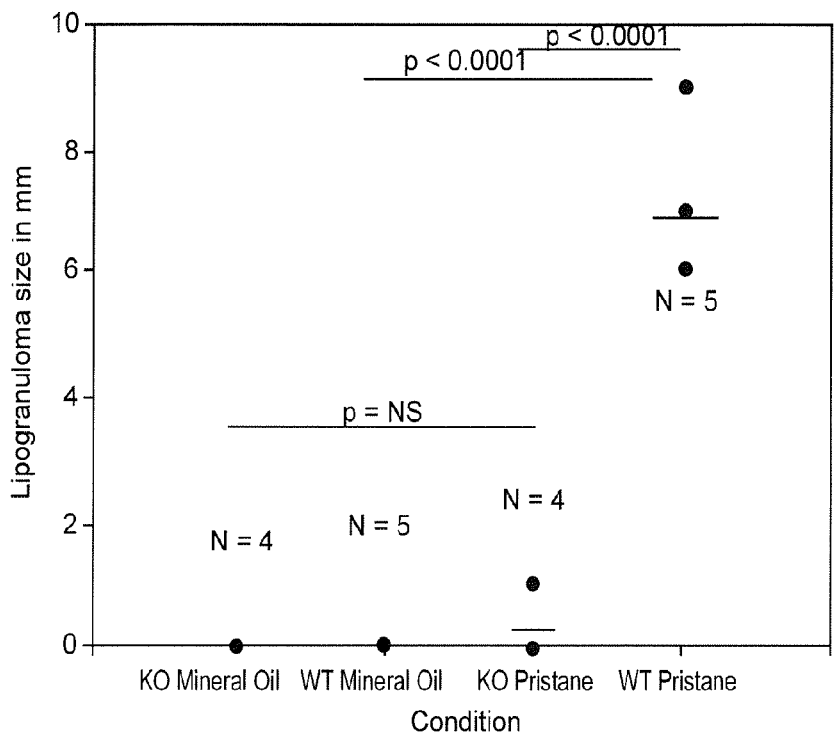
FIG. 9. KAR KO mice have reduced lipogranuloma formation following pristane induced lupus. 16 weeks after pristane injection, mice were sacrificed and lipogranulomas were excised. No noticeable tumor formation was observed in any of the mineral oil treated mice. Tumors were measured at the widest part of the tumor using calipers.
Figure 10:
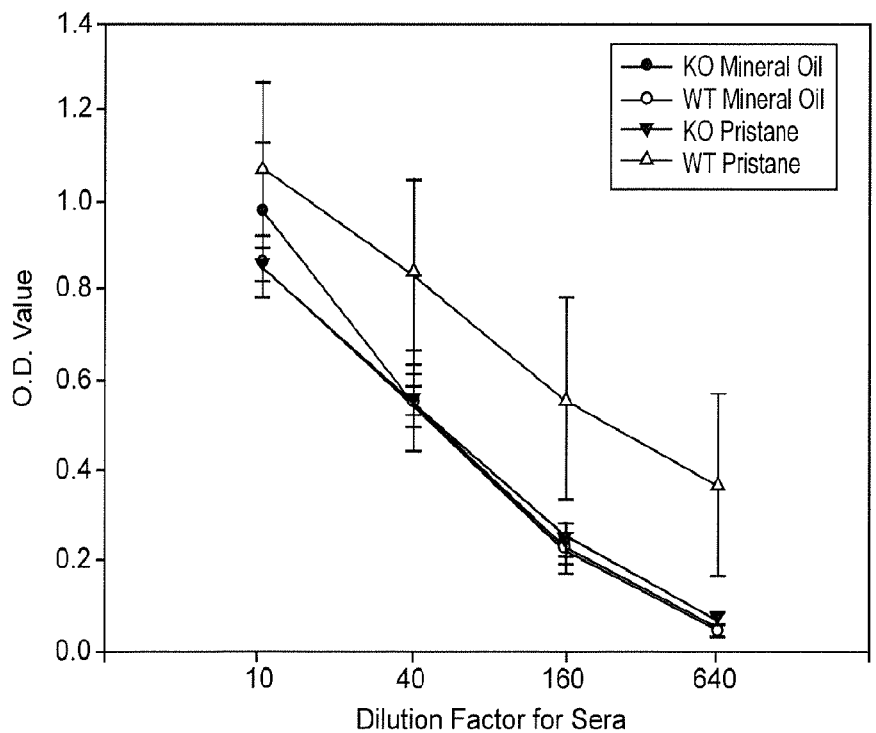
FIG. 10. KAR KO mice have reduced autoantibody production following pristane induced lupus. At the time of sacrifice, mice were cardiac punctured to obtain serum. Serum was analyzed for the presence of anti-snRNP/Sm antibodies. Briefly, a Nunc 96 well ELISA plate was coated with 5 μg/mL purified RNP/Sm antigen (The Binding Site). Serum was added in serial dilution and detected with a goat anti-mouse IgG horse radish peroxidase at a 1:5000 dilution.

We next wanted to determine the role, if any, KARs could play in the development of the exemplary autoimmune disease lupus. Because these mice are not genetically prone to this disease, we utilized the pristane induced model. This model which is well documented is known to induce a chronic inflammatory response when the chemical is introduced intraperitoneally resulting in a lupus-like disease in mice (Rev in (Reeves et al., 2009)). We injected age and sex matched 4 month old KAR KO or littermate controls with either mineral oil, as a control, or pristane and allowed the mice to age an additional 16 weeks. At the end of the 16 week period, the mice were sacrificed and examined for tumor formation at the site of injection, as well as autoantibody formation. The pristane lupus model is well established and a primary characteristic is a lipogranuloma formation at the site of the pristane injection. As shown in FIG. 9, all of the littermate controls (5 total) developed a significant lipogranuloma at the site of injection, as would be expected from the model. In contrast, lipogranuloma formation at the pristane injection site was quite minimal in the KAR knockout animals. In addition, the peritoneum had obvious signs of inflammation (observational data) in only the littermate control group treated with pristane. Analysis for anti-snRNP/Smith antigen also showed a clear trend towards increased autoantibody formation in the littermate controls as the autoantibody levels in the KAR KO mice were indistinguishable from either the KAR KO or littermate control (WT) animals given mineral oil (FIG. 10).

These data confirm that the KAR has a significant in vivo role and thus helps to establish this receptor as a viable drug target. These data further demonstrate that the KAR knockout mice are much less susceptible to pristane induced lupus. Taken together, these data strengthen the argument that KAR activation may be linked to exacerbated SLE pathology and through the use of specific pharmacological approaches, may serve as a novel therapeutic target for human disease.

Example 3

Examination of B Cells from Patients with SLE

Peripheral blood from both SLE patients and normal donors is obtained. Presence of KARS: Specific KAR primers and Western protocols are used to analyze mRNA and protein expression, respectively, in cultured B cells from SLE patients. Flow cytometry is used to confirm cell surface expression. Comparison of the expression of KARs on B cells from normal vs. SLE patients, the presence of KARs on SLE patient B cells is confirmed.

ADAM10 Levels:

Upon stimulation of KARs on B cells, levels of ADAM10 mRNA are examined in SLE and normal patient B cells via qPCR, and ADAM10 protein is detected via Western blot analysis. After treatment with either the natural KAR ligand glutamate or the exogenous ligand KA, cells from both groups are harvested and either RNA is isolated via standard Trizol protocol or protein is isolated via NP40 mediated cell lysis. RNA and protein are subjected to appropriate analysis. The data shows whether SLE patients have a higher basal expression of ADAM10 and whether ex vivo stimulation results in different amounts of ADAM10 between the two patient populations.

CD23 Levels:

CD23 expression on cells ex vivo directly from the patients is examined. Specific CD23 mAbs, human Fc receptor blocking agents and flow cytometric analysis are used to determine precise CD23 surface levels on cells. CD23 expression profiles are determined in specific subsets of cells in normal vs. SLE patients. CD23 release from cells stimulated in culture si also examined. B cells isolated from PBMC are cultured in the presence of either glutamate or KA for 24 hours. After overnight incubation, cell free supernatants are analyzed for sCD23 levels by ELISA, enabling determination of whether ex vivo stimulation results in differences in the amount of sCD23 released from B cells between the two patient populations. Lastly, as CD23 is cleaved by ADAM10 this aspect of B cell biology serves an additional purpose as direct measure of ADAM10 activity in the presence or absence of KAR stimulation.

Proliferation:

B cells isolated from both donor populations are stimulated with anti-CD40 in the presence or absence of KAR activation to induce cellular proliferation. Differences among both groups both with and without KAR stimulation are determined. Proliferation is measured via $H^3$ thymidine incorporation as well as cell cycle divisions via CFSE dilution analysis.

Ig Production:

B cells isolated from both populations are put in culture in the presence of IL-4 and anti-CD40, the two signals required for Ig production, in the presence or absence of KAR activation. After 14 days of culture, cell free supernatants are analyzed for total IgM, IgG, and IgE via ELISA. Furthermore, specificity of human antibodies is determined by employing commercially available human anti-nuclear antibody (ANA), anti-snRNP/Smith, and anti-dsDNA ELISA kits.

Antagonists:

SLE vs. normal donor B cell activity is compared in the presence of at least one antagonist such as NS 102. KAR antagonism overcomes the B cell hyperactivity seen in SLE patients.

Example 4

The Role of KARs in the Murine System

The role of KARs in the murine system is investigated using a well known lupus susceptible strain, the MRL/MpJ-Faslpr/J (KAR knockout mice) with pharmacological blockage of KARs. Mice are age matched and female as to eliminate any differences due to sex hormones or aging of the immune system. Before any drug administration, 5 animals/group are sacrificed in order to establish a baseline "lupus panel" (See Table 1). At 7 weeks of age, approximately one half of the remaining test animals are given vehicle (DMSO) and the remaining half are administered NS 102 using a standard dosing regimen used in rodent models. After treatment initiation, 5 mice per group are examined at weeks 8, 10, 12, 14, 16, 18 and 20. Continuation of the study to the 20 week mark, enables determination of whether KAR blockade affects mean survival time as the MRL/MpJ-Faslpr/J have a reported average life span of 17 weeks due to severe glomerulonephritis.

This study determines that in vivo kainate receptor blockade alleviates immunopathology associated with SLE.

TABLE 1

| Organ System | Parameter | Method |
|---|---|---|
| Skeletal | Arthritis | Immunohistochemistry of inflamed joints |
| Immune | Abnormal Lymph Nodes | Measurement of size and cellularity of draining lymph nodes from areas with visible inflammation |
| | Abnormal Spleen | Measurement of size and cellularity |
| | Antibody Levels | ELISAs to determine levels of various Ig subclasses and to detect presence of ANA, anti-snRNP/Smith, and anti dsDNA abs |
| | Acute Phase Response | ELISAs to measure C reactive protein levels |
| Renal | Glomerulonephritis | Examine immune complex deposition via immunohistochemistry |
| Skin/Coat/Nails | Skin Lesions | Physical Examination |
| Nervous | CNS involvement | Seizure activity and/or behavioral changes through observation |
| Mortality | Premature Death | Measure Survival of animals |

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Aitken, K. J. (2008). Intersubjectivity, affective neuroscience, and the neurobiology of autistic spectrum disorders: a systematic review. Keio J. Med. 57, 15-36.

Boldyrev, A. A., Carpenter, D. O., and Johnson, P. (2005). Emerging evidence for a similar role of glutamate receptors in the nervous and immune systems. J. Neurochem. 95, 913-918.

Boldyrev, A. A., Kazey, V. I., Leinsoo, T. A., Mashkina, A. P., Tyulina, O. V., Johnson, P., Tuneva, J. O., Chittur, S., and Carpenter, D. O. (2004). Rodent lymphocytes express functionally active glutamate receptors. Biochem. Biophys. Res. Commun. 324, 133-139.

Borsody, M. K. and Coco, M. L. (2001). A hypothesis accounting for the inconsistent benefit of glucocorticoid therapy in closed head trauma. Med. Hypotheses. 56, 65-72.

Briel et al. (2010) European Journal of Medicinal Chemistry 45, 69-77.

Caven, T. H., Shelburne, A., Sato, J., Chan-Li, Y., Becker, S., and Conrad, D. H. (2005b). IL-21 dependent IgE production in human and mouse in vitro culture systems is cell density and cell division dependent and is augmented by IL-10. Cell Immunol. 238, 123-134.

Caven, T. H., Shelburne, A., Sato, J., Becker, S., and Conrad, D. H. (2005a). IL-21 dependent IgE production in human and mouse in vitro culture systems is cell density and cell division dependent and is augmented by IL-10. Cell Immunol. 238, 123-134.

Caven, T. H., Sturgill, J. L., and Conrad, D. H. (2007). BCR ligation antagonizes the IL-21 enhancement of anti-CD40/IL-4 plasma cell differentiation and IgE production found in low density human B cell cultures. Cell Immunol. 247, 49-58.

Collingridge, G. L., Olsen, R. W., Peters, J., and Spedding, M. (2009). A nomenclature for ligand-gated ion channels. Neuropharmacology. 56, 2-5.

Du, Y., Li, C., Hu, W. W., Song, Y. J., and Zhang, G. Y. (2009). Neuroprotection of preconditioning against ischemic brain injury in rat hippocampus through inhibition of the assembly of GluR6-PSD95-mixed lineage kinase 3 signaling module via nuclear and nonnuclear pathways. Neuroscience. 161, 370-380.

Eck, H. P., Betzler, M., Schlag, P., and Droge, W. (1990). Partial recovery of lymphocyte activity in patients with colorectal carcinoma after curative surgical treatment and return of plasma glutamate concentrations to normal levels. J. Cancer Res. Clin. Oncol. 116, 648-650.

Eck, H. P., Frey, H., and Droge, W. (1989). Elevated plasma glutamate concentrations in HIV-1-infected patients may contribute to loss of macrophage and lymphocyte functions. Int. Immunol. 1, 367-372.

Flood, S., Williams, A., Duance, V., and Mason, D. (2007). Modulation of interleukin-6 and matrix metalloproteinase 2 expression in human fibroblast-like synoviocytes by functional ionotropic glutamate receptors. Arthritis Rheum. 56, 2523-2534.

Ford, J. W., Kilmon, M. A., Haas, K. M., Shelburne, A. E., Chan-Li, Y., and Conrad, D. H. (2006). In vivo murine CD23 destabilization enhances CD23 shedding and IgE synthesis. Cell Immunol. 243, 107-117.

Fridman, J. S., Caulder, E., Hansbury, M., Liu, X., Yang, G., Wang, Q., Lo, Y., Zhou, B. B., Pan, M., Thomas, S. M., Grandis, J. R., Zhuo, J., Yao, W., Newton, R. C., Friedman, S. M., Scherle, P. A., and Vaddi, K. (2007). Selective inhibition of ADAM metalloproteases as a novel approach for modulating ErbB pathways in cancer. Clin. Cancer Res. 13, 1892-1902.

Ganor, Y., Besser, M., Ben-Zakay, N., Unger, T., and Levite, M. (2003b). Human T cells express a functional ionotropic glutamate receptor GluR3, and glutamate by itself triggers integrin-mediated adhesion to laminin and fibronectin and chemotactic migration. J. Immunol. 170, 4362-4372.

Ganor, Y., Besser, M., Ben-Zakay, N., Unger, T., and Levite, M. (2003a). Human T cells express a functional ionotropic glutamate receptor GluR3, and glutamate by itself triggers integrin-mediated adhesion to laminin and fibronectin and chemotactic migration. J. Immunol. 170, 4362-4372.

Haas, H. S., Pfragner, R., Siegl, V., Ingolic, E., Heintz, E., and Schauenstein, K. (2005). Glutamate receptor-mediated effects on growth and morphology of human histiocytic lymphoma cells. Int. J. Oncol. 27, 867-874.

Hasbold, J., Lyons, A. B., Kehry, M. R., and Hodgkin, P. D. (1998). Cell division number regulates IgG1 and IgE switching of B cells following stimulation by CD40 ligand and IL-4. Eur. J. Immunol. 28, 1040-1051.

Hou, Y. Y., Liu, Y., Kang, S., Yu, C., Chi, Z. Q., and Liu, J. G. (2009). Glutamate receptors in the dorsal hippocampus mediate the acquisition, but not the expression, of conditioned place aversion induced by acute morphine withdrawal in rats. Acta Pharmacol. Sin. 30, 1385-1391.

Kaczor et al. (2009) J. Chem. Inf. Moedl. 49, 1094-1104.

Lerma, J. (2006). Kainate receptor physiology. Curr. Opin. Pharmacol. 6, 89-97.

Lerma, J., Paternain, A. V., Rodriguez-Moreno, A., and Lopez-Garcia, J. C. (2001). Molecular physiology of kainate receptors. Physiol Rev. 81, 971-998.

McNearney, T., Speegle, D., Lawand, N., Lisse, J., and Westlund, K. N. (2000). Excitatory amino acid profiles of synovial fluid from patients with arthritis. J. Rheumatol. 27, 739-745.

Mulle, C., Sailer, A., Perez-Otano, I., ckinson-Anson, H., Castillo, P. E., Bureau, I., Maron, C., Gage, F. H., Mann, J. R., Bettler, B., and Heinemann, S. F. (1998). Altered synaptic physiology and reduced susceptibility to kainate-induced seizures in GluR6-deficient mice. Nature. 392, 601-605.

Ortiz, R. M., Karkkainen, I., Huovila, A. P., and Honkaniemi, J. (2005). ADAM9, ADAM10, and ADAM15 mRNA levels in the rat brain after kainic acid-induced status epilepticus. Brain Res. Mol. Brain Res. 137, 272-275.

Payet-Jamroz, M., Helm, S. L., Wu, J., Kilmon, M., Fakher, M., Basalp, A., Tew, J. G., Szakal, A. K., Noben-Trauth, N., and Conrad, D. H. (2001). Suppression of IgE responses in CD23-transgenic animals is due to expression of CD23 on nonlymphoid cells. J Immunol 166, 4863-4869.

Rabah, D. and Conrad, D. H. Effect of Cell Density on in vitro mouse IgE production. 2002. Ref Type: Unpublished Work Raber, J. (1998). Detrimental effects of chronic hypothalamic-pituitary-adrenal axis activation. From obesity to memory deficits. Mol. Neurobiol. 18, 1-22.

Rainesalo, S., Keranen, T., Palmio, J., Peltola, J., Oja, S. S., and Saransaari, P. (2004). Plasma and cerebrospinal fluid amino acids in epileptic patients. Neurochem. Res. 29, 319-324.

Rawls, S. M., Thomas, T., Adeola, M., Patil, T., Raymondi, N., Poles, A., Loo, M., and Raffa, R. B. (2009). Topiramate antagonizes NMDA- and AMPA-induced seizure-like activity in planarians. Pharmacol. Biochem. Behav. 93, 363-367. 26

Reeves, W. H., Lee, P. Y., Weinstein, J. S., Satoh, M., and Lu, L. (2009) Trends Immunol. 30, 455-464

Saxon, A., Ke, Z., Bahati, L., and Stevens, R. H. (1990). Soluble CD23 containing B cell supernatants induce IgE from peripheral blood B-lymphocytes and costimulate with interleukin-4 in induction of IgE. J. Allergy Clin. Immunol. 86, 333-344.

Sun, H., Swaim, A., Herrera, J. E., Becker, D., Becker, L., Srivastava, K., Thompson, L. E., Shero, M. R., Perez-Tamayo, A., Suktitipat, B., Mathias, R., Contractor, A., Faraday, N., and Morrell, C. N. (2009). Platelet kainate receptor signaling promotes thrombosis by stimulating cyclooxygenase activation. Circ. Res. 105, 595-603.

Szklarczyk, A., Lapinska, J., Rylski, M., McKay, R. D., and Kaczmarek, L. (2002). Matrix metalloproteinase-9 undergoes expression and activation during dendritic remodeling in adult hippocampus. J Neurosci. 22, 920-930.

Verdoom, T. A., Johansen, T. H., Drejer, J., and Nielsen, E. O. (1994). Selective block of recombinant glur6 receptors by NS-102, a novel non-NMDA receptor antagonist. Eur. J. Pharmacol. 269, 43-49.

Weskamp, G., Ford, J. W., Sturgill, J., Martin, S., Docherty, A. J., Swendeman, S., Broadway, N., Hartmann, D., Saftig, P., Umland, S., Sehara-Fujisawa, A., Black, R. A., Ludwig, A., Becherer, J. D., Conrad, D. H., and Blobel, C. P. (2006). ADAM10 is a principal 'sheddase' of the low-affinity immunoglobulin E receptor CD23. Nat. Immunol. 7, 1293-1298.

West, S. G. (2007). The Nervous System. In Dubois' lupus erythematosus, D. J. Wallace, B. Hahn, and E. L. Dubois, eds. (Philadelphia: Lippincott Wiliams and Wilkins), pp. 707-747.

Zhou, B. B., Peyton, M., He, B., Liu, C., Girard, L., Caudler, E., Lo, Y., Baribaud, F., Mikami, L, Reguart, N., Yang, G., Li, Y., Yao, W., Vaddi, K., Gazdar, A. F., Friedman, S. M., Jablons, D. M., Newton, R. C., Fridman, J. S., Minna, J. D., and Scherle, P. A. (2006). Targeting ADAM mediated ligand cleavage to inhibit HER3 and EGFR pathways in non-small cell lung cancer. Cancer Cell. 10, 39-50.

We claim:

1. A method of treating an allergy or an autoimmune disease selected from the group consisting of systemic lupus erthyematosus (SLE), rheumatoid arthritis, and Sjogren's syndrome in a patient in need thereof, comprising the step of
administering to said patient an agent that is 5-nitro-6,7,8,9-tetrahydro-1H-benzo[g]indole-2,3-dione 3-oxime (NS-102), wherein said agent is administered in a form and under conditions which permit binding to a kainate receptor (KAR), and which prevent or reduce glutamate binding to said KAR, so as to reduce B cell proliferation in said patient.

2. The method of claim 1, further comprising the step of identifying a patient with symptoms of said allergy or said autoimmune disease prior to said step of administering.

3. The method of claim 1, further comprising the step of monitoring symptoms of said allergy or said autoimmune disease after said step of administering.

4. A method of treating an allergy in a patient in need thereof, comprising the step of
administering to said patient an agent that is 5-nitro-6,7,8,9-tetrahydro-1H-benzo[g]indole-2,3-dione 3-oxime (NS-102), wherein said agent is administered in a form and under conditions which permit binding to a kainate receptor (KAR), and which prevent or reduce glutamate binding to said KAR, so as to reduce B cell proliferation in said patient.

5. A method of treating an autoimmune disease selected from the group consisting of systemic lupus erthyematosus (SLE), rheumatoid arthritis, and Sjogren's syndrome in a patient in need thereof, comprising the step of
administering to said patient an agent that is 5-nitro-6,7,8,9-tetrahydro-1H-benzo[g]indole-2,3-dione 3-oxime (NS-102), wherein said agent is administered in a form and under conditions which permit binding to a kainate receptor (KAR), and which prevent or reduce glutamate binding to said KAR, so as to reduce B cell proliferation in said patient.

* * * * *